(12) United States Patent
Epstein et al.

(10) Patent No.: US 10,874,453 B2
(45) Date of Patent: Dec. 29, 2020

(54) MERGED IMAGE USER INTERFACE AND NAVIGATIONAL TOOL FOR REMOTE CONTROL OF SURGICAL DEVICES

(75) Inventors: Gordon Epstein, Austin, TX (US); Richard Spero, Austin, TX (US)

(73) Assignee: ACESSA HEALTH INC., Austin, TX (US)

( * ) Notice: Subject to any disclaimer, the term of this patent is extended or adjusted under 35 U.S.C. 154(b) by 0 days.

(21) Appl. No.: 13/069,497

(22) Filed: Mar. 23, 2011

(65) Prior Publication Data

US 2012/0245576 A1   Sep. 27, 2012

(51) Int. Cl.
*A61B 18/14*   (2006.01)
*A61B 18/00*   (2006.01)
(Continued)

(52) U.S. Cl.
CPC ...... *A61B 18/1487* (2013.01); *A61B 18/1477* (2013.01); *A61B 2017/00212* (2013.01); *A61B 2018/00559* (2013.01); *A61B 2018/00577* (2013.01); *A61B 2018/00589* (2013.01); *A61B 2018/00642* (2013.01); *A61B 2018/00708* (2013.01); *A61B 2018/00797* (2013.01); *A61B 2018/00821* (2013.01); *A61B 2018/00982* (2013.01); *A61B 2018/143* (2013.01); *A61B 2090/378* (2016.02)

(58) Field of Classification Search
CPC ............ A61B 18/1487; A61B 18/1477; A61B 2018/00821; A61B 2018/143; A61B 2018/00559; A61B 2018/00577; A61B 2018/00642; A61B 2018/00708; A61B 2018/00589; A61B 2018/00797; A61B 2018/00982; A61B 2090/378

USPC ............... 606/41–52; 434/262, 267
See application file for complete search history.

(56) References Cited

U.S. PATENT DOCUMENTS 5,540,681 A * 7/1996 Strul et al. ...................... 606/34
6,192,266 B1 * 2/2001 Dupree ................ A61B 5/0422
                                                       600/427

(Continued)

OTHER PUBLICATIONS

Bergamini, MD. et al. "Laparoscopic radiofrequency thermal ablation: A new approach to symptomatic uterine myomas," American Journal of Obstetrics and Gynecology, 192:768-73 Varese, Italy, Mar. 1, 2005.

*Primary Examiner* — Eun Hwa Kim
(74) *Attorney, Agent, or Firm* — Vista IP Law Group, LLP

(57) ABSTRACT

The invention provides a system for remote control of a surgical device, comprising a first imaging device of a first type having a first image output. The first imaging device is positioned to image an area being subject to surgery. A second imaging device of a second type has a second image output. The second imaging device is positioned to image the area being subjected to surgery. A computer is coupled to receive the first and second image outputs and merge the first and second image outputs into a unitary image output representing a unitary image. Software, resident in the computer generates a graphic user interface including a menu and submenu items. A surgical device is coupled to the computer. Software, resident in said computer, receives and displays information received from the surgical device and/or controls the operation of the surgical device. A display as coupled to the computer for displaying the graphic user interface and the unitary image.

17 Claims, 44 Drawing Sheets

(51) Int. Cl.
*A61B 17/00* (2006.01)
*A61B 90/00* (2016.01)

(56) References Cited

U.S. PATENT DOCUMENTS

| | | | |
|---|---|---|---|
| 6,273,886 B1* | 8/2001 | Edwards et al. | 606/34 |
| 6,622,731 B2* | 9/2003 | Daniel et al. | 128/898 |
| 6,840,935 B2* | 1/2005 | Lee | A61B 17/42 |
| | | | 128/898 |
| 7,285,117 B2* | 10/2007 | Krueger | A61B 18/00 |
| | | | 600/374 |
| 7,452,357 B2* | 11/2008 | Vlegele et al. | 606/32 |
| 7,480,533 B2* | 1/2009 | Cosman | A61B 18/1477 |
| | | | 606/21 |
| 2001/0035871 A1* | 11/2001 | Bieger et al. | 345/630 |
| 2003/0199864 A1* | 10/2003 | Eick | 606/41 |
| 2006/0155577 A1* | 7/2006 | Niemeyer | 705/2 |
| 2009/0187182 A1* | 7/2009 | Epstein | A61B 18/1477 |
| | | | 606/34 |
| 2010/0063509 A1* | 3/2010 | Borja et al. | 606/88 |

\* cited by examiner

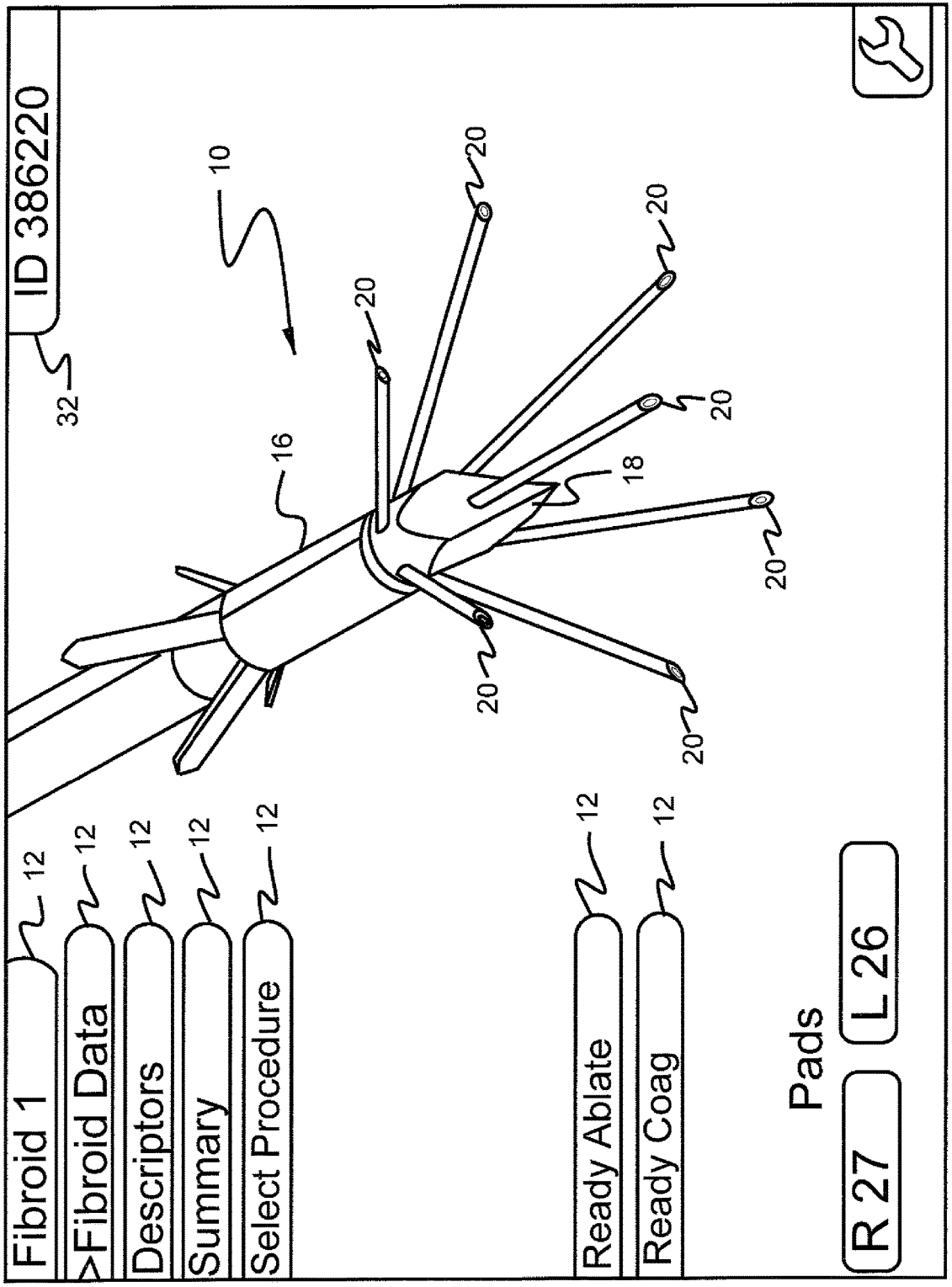

MERGED IMAGE USER INTERFACE AND NAVIGATIONAL TOOL FOR REMOTE CONTROL OF SURGICAL DEVICES

FIELD OF THE INVENTION

The invention relates to a control mechanism for a medical device positioned in a patient's body for ablation of a tumor, such as a uterine fibroid and, more particularly, to a control button array for navigation through a graphical user interface for remotely controlling a source of radio frequency (RF) energy coupled to an ablation probe during a surgical procedure while maintaining the sterile field.

BACKGROUND OF THE INVENTION

Advances in technology have resulted in systems that allow a practitioner or other medical professional to remotely control the operation of a medical device. Current devices control an ablation device by direct control of a number of parameters through the use of a matrix of buttons on the face of an RF power generator. These buttons include a pair of buttons labeled with up arrow and down arrow markings to control the setting of temperature which is displayed on a digital meter proximate thereto. A similar pair of buttons is used to control the setting of time. Operation of the buttons to adjust temperature, time and other RF generator functions controlled by the matrix of controls on the front panel of the generator may be performed by a nurse or other person assisting the surgeon. The application of RF energy is controlled by a foot pedal.

SUMMARY OF THE INVENTION

In accordance with the invention, a system is provided for remote control of a surgical device, comprising a first imaging device of a first type having a first image output. The first imaging device is positioned to image an area being subject to surgery. A second imaging device of a second type has a second image output. The second imaging device is positioned to image the area being subjected to surgery. A computer is coupled to receive the first and second image outputs and merge the first and second image outputs into a unitary image output representing a unitary image. Software, resident in the computer generates a graphic user interface including a menu and submenu items. A surgical device is coupled to the computer. Software, resident in said computer, receives and displays information received from the surgical device and/or controls the operation of the surgical device. A display as coupled to the computer for displaying the graphic user interface and the unitary image.

The inventive ablation device may be controlled by using a simplified button array in conjunction with a graphical user interface ("GUI"). The inventive GUI graphically portrays a uterine ablation probe which allows the physician to visualize the procedure as well as the parameters of each step in the ablation process and results.

The advantage of the inventive GUI-based system over conventional alpha-numeric controls is the ability to visually display the device's operating parameters in an intuitive fashion, together with medical data associated with the particular patient. At the same time, the inventive device provides for an intuitive and simplified means to control the application of ablation energy. In this way, the device is easier to use and configure, and provides the surgeon with a better picture of the procedure and the data relative to the operation of the device.

At the same time, during the ablation of tumors, such as uterine fibroids, it would be advantageous to provide a means for recording information relating to the particular surgery being performed.

Currently, however, there is no effective methodology for allowing a surgeon to control remotely an ablation device used to control an RF ablation probe. In accordance with the invention, this is achieved via the use of a graphical user interface employed during the surgical procedure in a manner calculated to reduce the likelihood of breaking the sterility of the surgical field.

There exists a need, therefore, for a system and method which allows a surgeon to remotely control a medical device and to input data, collect data, make surgical choices and perform surgery with the intuitive interface provided by a graphical user interface without breaking the sterile field.

The present invention fulfills this need by providing a system and method for a surgeon to remotely control a radiofrequency (RF) ablation device, view operating parameters and record information associated with the procedure during a surgery to ablate a tissue mass such as a uterine fibroid tumor. In particular, such control is achieved in a multiple stylet ablation system, in which each stylet incorporates temperature monitoring componentry. The operating parameters of the components of the ablation device are controlled by a computer in accordance with software which controls the power applied to the ablation device in response to feedback temperature information taken at the tissue area being operated on and/or in accordance with a preset program. Such program may involve the application of a particular amount of energy for a particular length of time, when that option is selected by the surgeon.

More particularly, the invention provides a system and method for a practitioner to remotely operate a RF ablation device using a pair of buttons and a GUI which displays a hierarchical system of menu and submenu choices. The GUI provides information both prior to and during a surgical procedure to ablate and coagulate a tissue mass, and, in particular, a uterine fibroid tumor. The surgeon achieves the desired control using a two button electronic control system mounted on the handle of the ablation probe then using a foot pedal. This allows the achievement of the desired degree of control, with ease and speed, due to the easy accessibility of all controls. At the same time, the controls are substantially placed in close proximity to operators for extending the ablation of stylets and an operator for controlling use of anchoring members. As a result the same may be achieved without breaking sterility of the surgical field.

The inventive system and method comprises an ablation device, a general purpose personal computer (which may be housed in a dedicated housing which may also incorporate specialized controls which are particular to an ablation system, such as RF generator controls which may be used, for example, to override control signals produced by the computer, prior art RF generator displays and so forth. The system is controlled by a software program, which produces a GUI. The ablation probe comprises operators for advancing and retracting ablation stylets, an operator for advancing and retracting anchor members, and a navigational button array for allowing a surgeon to scroll and select through a series of menu and submenu choices displayed on the GUI.

The menus and submenus allow for the entry of patient data, as well as for the control of certain parameters and operation of the ablation device. The inventive system and method also comprises a foot pedal used by the practitioner for operating the ablation device to ablate and coagulate a tissue mass in a patient.

The ablation device comprises a trocar and a plurality of stylets, i.e., RF ablation electrodes, which are located at the tip of a trocar and conduct radiofrequency energy to a tissue mass to be ablated, such as a uterine fibroid. During a surgical procedure, the tip of the trocar of the ablation device is deployed within a tissue mass in a patient. Electrical current travels through the trocar, the tissue mass to be ablated, and to a right and a left pad placed atop the right and the left leg of the patient, respectively. The temperature of the right and the left pads are also advantageously displayed on the GUI. The GUI may also indicate tissue temperature adjacent each stylet, or alternatively other measures of stylet and adjacent tissue temperature, for example, the average, the highest temperature, the lowest temperature, or the average of all the stylet temperatures after factoring out the highest and lowest temperatures. Generally, it is noted that the stylet temperature is indicative of the temperature reached by the tissue adjacent to the particular stylet of the ablation device.

The ablation device probe comprises a navigational button matrix for navigating through the GUI. The navigational button matrix comprises a scroll button and a select button that interacts with computer software displayed on the GUI. Depressing the scroll button (which may be configured with two raised dots on the button surface) moves through closed loop menus which are associated with submenus which are displayed on the GUI when the menu item is highlighted. Depressing the select button (which may be configured as one raised dot on the navigational button matrix) selects a desired menu or submenu. To return to a particular menu choice, the practitioner scrolls through the menu choices rather than hitting a back button, as will be described in detail below.

In accordance with a preferred alternative of the present invention the screen displaying menu and submenu options is a touchscreen, which may directly receive selections. In accordance with this alternative, the surgeon has the option of making choices on the GUI by asking an assistant to operate the touchscreen directly, rather than using the navigational tool. Under normal operating conditions, it is anticipated that the surgeon would do the bulk of the control using the button matrix, but in emergency the surgeon may elect to directly operate the touchscreen, albeit at the risk of disrupting the sterility of the surgical field.

The menu choices for selection displayed on the GUI may include, by way of example, fibroid data, descriptors, summary, select procedure, ready ablate and ready coag choices. The fibroid data menu has submenu choices which include, for example, number, diameter, position and type. The diameter choices include diameters ranging from less than 1 cm to 15 cm. The position choices include, for example, anterior, posterior and lateral positions. The anterior, posterior and lateral position choices each has submenus which include, for example, midline, right and left choices. The submenu for midline, right and left choices each has further submenus which include, for example, fundal, mid-uterine, lower segment and cervical choices. The submenu for fundal, mid-uterine, lower segment and cervical choices each has further submenus which include, for example, intramural, subserosal, submucous 1 and submucous 2 choices. The select procedure menu may have submenus which include, for example, temperature (where the software control system is programmed to reach and maintain a desired temperature), manual and impedance (where the software controls the system to shut down if higher impedances corresponding to the RF energy beginning to char the tissue are detected) choices.

In accordance with the invention, the practitioner selects a target temperature to which the tissue mass will be subjected during surgery prior to the start of ablation of the tissue mass. The choice of temperatures ranges from 90 degrees centigrade to 100 degrees centigrade. The ablation of the tissue mass is achieved by selecting the ready ablate menu and the confirm submenu choice. To start ablation of the tissue mass, the practitioner presses and releases a foot pedal which controls radiofrequency energy sent to the plurality of stylets of the ablation device. To stop ablation of the tissue mass, the practitioner again presses and releases the foot pedal. Initiation of ablation of the tissue mass causes temperature in the tissue mass adjacent to each of the plurality of stylets of the ablation device to increase up to the preset target temperature. An average temperature of the tissue mass calculated from two or more of the plurality of stylets of the ablation device is displayed on the GUI.

The time elapsed from the start of ablation is displayed as "ramp time" on the GUI. The time elapsed once the temperature of the tissue mass has reached the preset target temperature, calculated, for example, by taking an average of the temperatures provided by the stylets, is displayed as "target time" on the GUI. This is the length of time that the surgeon has decided is necessary for the stylet to be at the selected temperature, for example, in order to achieve the desired ablation zone. The target time can range from about 10 seconds to about 20 minutes depending on the size of the tissue mass being ablated and the deployment of the ablation device. The total time elapsed from the start of ablation to the end of ablation is displayed as "total time" on the GUI.

Manual choices include selecting a target power level, which is the power level of radiofrequency energy, emitted by the plurality of stylets and trocar. Target power levels range from about 10 watts to about 100 watts. In accordance with the invention, the practitioner chooses a target power level prior to starting ablation of the tissue mass.

Coagulation of the tissue track made by the entry of the trocar is achieved by selecting the menu "ready coag". To coagulate the tissue mass, the practitioner presses and holds the foot pedal which sends radiofrequency energy to the trocar of the ablation device. RF energy is applied to the trocar during withdrawal of the trocar from the patient in a conventional manner.

BRIEF DESCRIPTION OF THE DRAWINGS

A full understanding of the invention can be gained from the following description of the preferred embodiments when read in conjunction with the accompanying drawings in which:

FIG. 1c shows the graphical user interface screen in which menus "fibroid data", "descriptor", "summary", "select procedure", "ready ablate" and "ready coag" are displayed, and the navigational tool has scrolled to the menu choice "fibroid data";

DETAILED DESCRIPTION OF THE INVENTION

Figure 1A:
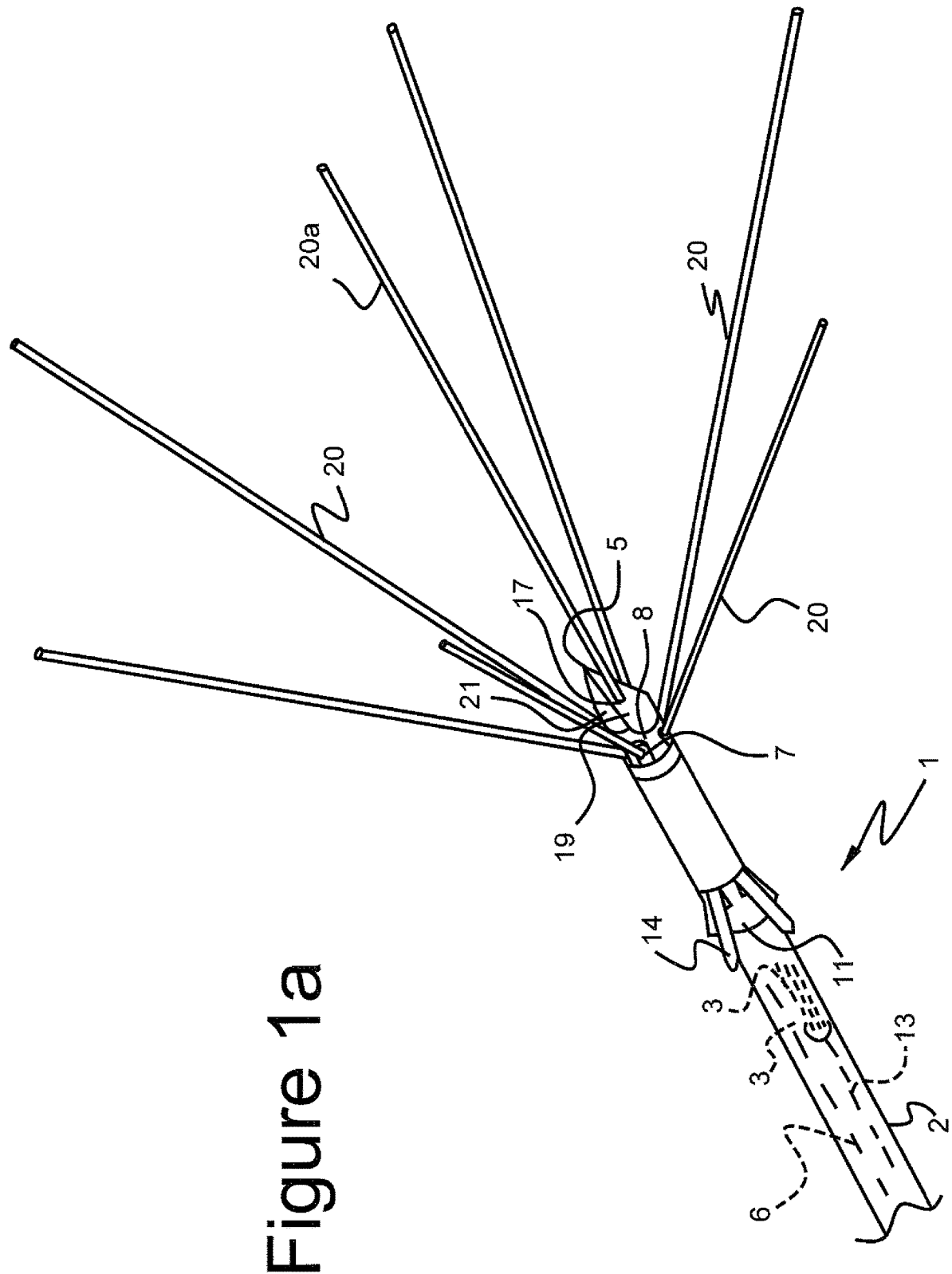
FIG. 1a illustrates an ablation device useful with the inventive system.

FIG. 1a is a perspective view of a multiple antennae or stylet ablation trocar instrument 1 useful in practicing the inventive system. Ablation instrument 1 comprises a cannula 2 which houses a plurality of stylets 20 and, optionally, a plurality of anchors 4. A trocar point 5 is provided at the distal end of cannula 2. At least one conductor 6 is provided within cannula 2. Conductor 6 is electrically coupled to stylets 20 and trocar point 4 and accordingly provides RF energy to stylets 20 and trocar point 5. In accordance with the invention, stylets 20 and trocar point 5 are electrically coupled to each other and electrically isolated from other exposed portions of ablation instrument 1. Stylets 20 and trocar point 5 are at the distal end of ablation instrument 1. Each of the stylets is made of thin wire-like tubular members and during the procedure is initially housed entirely within the cannula 2.

Stylets 20 are deployed for ablation by being advanced in the forward direction toward the distal end of ablation instrument 1 out from ablation instrument 1 through openings 7. As stylets 20 are advanced through openings 7, they bear against deflection surfaces 8. Deflection surfaces 8 are defined in the metal body which defines trocar point 5 at the distal end of the cannula 2.

During use of the inventive system, trocar point 5 at the distal end of cannula 2 is used to initially pierce the tissue of the fibroid tumor during use of the inventive ablation device 1. Optionally, a plurality of anchors 9, also housed within ablation instrument 1, may be deployed rearwardly toward the proximal end of ablation instrument 1. During deployment, anchors 9 are deflected by deflection surface 11 to move into the positions illustrated in FIG. 1. After deployment, anchors 9 may optionally be used to prevent rearward movement of trocar point 5 during deployment of stylets 20.

Figure 1B:
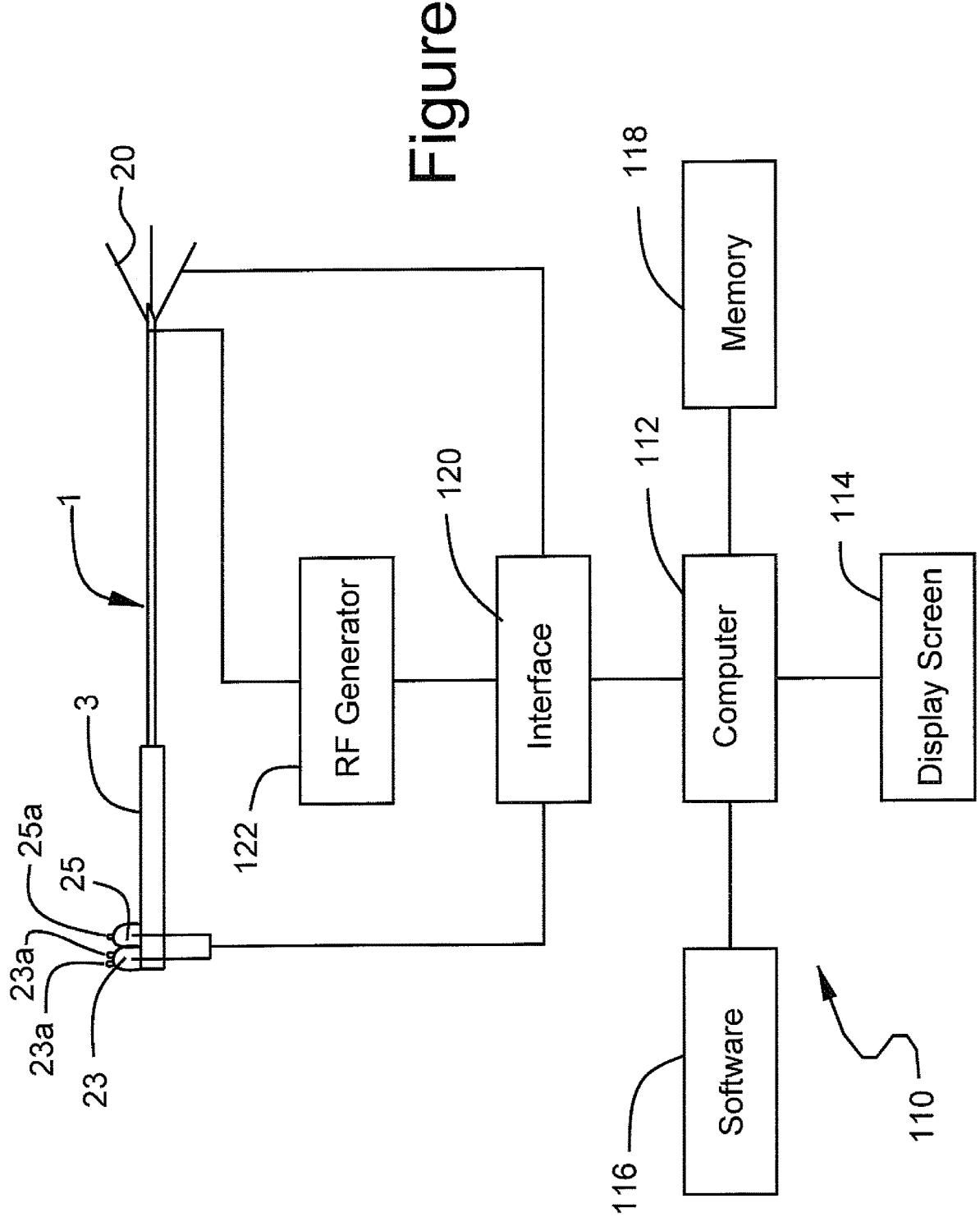
FIG. 1b illustrates an ablation system incorporating computer controls in accordance with the inventive system.

Stylets 20 are deployed through the use of a slideably mounted operator member 13 housed within cannula 2 and coupled to an operating handle at its proximal end. Anchors 9 are also deployed through the use of a slideably mounted operator member (not illustrated) housed within cannula 2 and coupled to an operating handle at its proximal end. The distal end of operator member 13 is coupled to stylets 3 which may thus be advanced an identical distance in unison. The retraction and deployment of anchors and stylets is controlled by an operator handle 3 as illustrated in FIG. 1b.

Referring to FIG. 1c, a graphical user interface (GUI) 10 display screen in accordance with the present invention is shown. In accordance with the preferred embodiment, a surgeon uses a medical device such as an ablation device. The ablation device is illustrated in GUI 10 by ablation device illustration 16. The ablation device is used for ablating tissue masses. Use of the same is facilitated by GUI 10 and the navigational button matrix to minimize the likelihood of breaking the sterility of the surgical field. The GUI 10 displays a choice of menu items 12 that the practitioner can scroll through by depressing the scroll button 23 (FIG. 1b) which carries two raised dots 23a on its surface on the navigational button matrix. All of the menu items 12 are displayed at the same time. The menu items 12 allow the surgeon or other practitioner to enter patient data, collect patient data and perform a surgical procedure all within the sterile field. When a desired menu is reached, the surgeon selects from menu items 12 by depressing the select button 25, which has one raised dot 25a on its top surface, on the navigational button matrix, which may be viewed as a whole as a navigational tool. In one preferred embodiment of the invention, when ablating a tissue mass such as a fibroid tumor, the menu 12 choices comprise the "Fibroid" number data, "Fibroid Data", "Descriptors", "Summary", "Select Procedure", "Ready Ablate" and "Ready Coag". In FIG. 1b, the system indicates that information with respect to a first fibroid, "Fibroid 1", is being collected. In FIG. 1, an arrow indicator 15 indicates that the surgeon has scrolled to the "Fibroid Data" menu item. Repeated depression of the scroll button causes the arrow indicator to move in sequence through the choices comprising menu items labeled "Fibroid" for the fibroid number, "Fibroid Data", "Descriptors", "Summary", "Select Procedure", "Ready Ablate" and "Ready Coag". Stopping on the fibroid number data which is labeled "Fibroid 1" in FIG. 1b (which results in placing the arrow indicator before the indication "Fibroid 1"), and depressing of the select button results in causing the arrow indicator to cursor through indicators reading "Fibroid 1", "Fibroid 2", "Fibroid 3", "Fibroid 4", "Fibroid 5" and so forth. If one next depresses the scroll button, arrow indicator 15 indicates selection of "Fibroid Data". As an alternative, one also can scroll to the "Fibroid Data", push select, scroll to the numbers until the desired fibroid number is presented (for example "Fibroid 2"), and click the select button resulting in the display of "Fibroid 2" instead of "Fibroid 1" as illustrated in FIG. 1.

Figure 2:
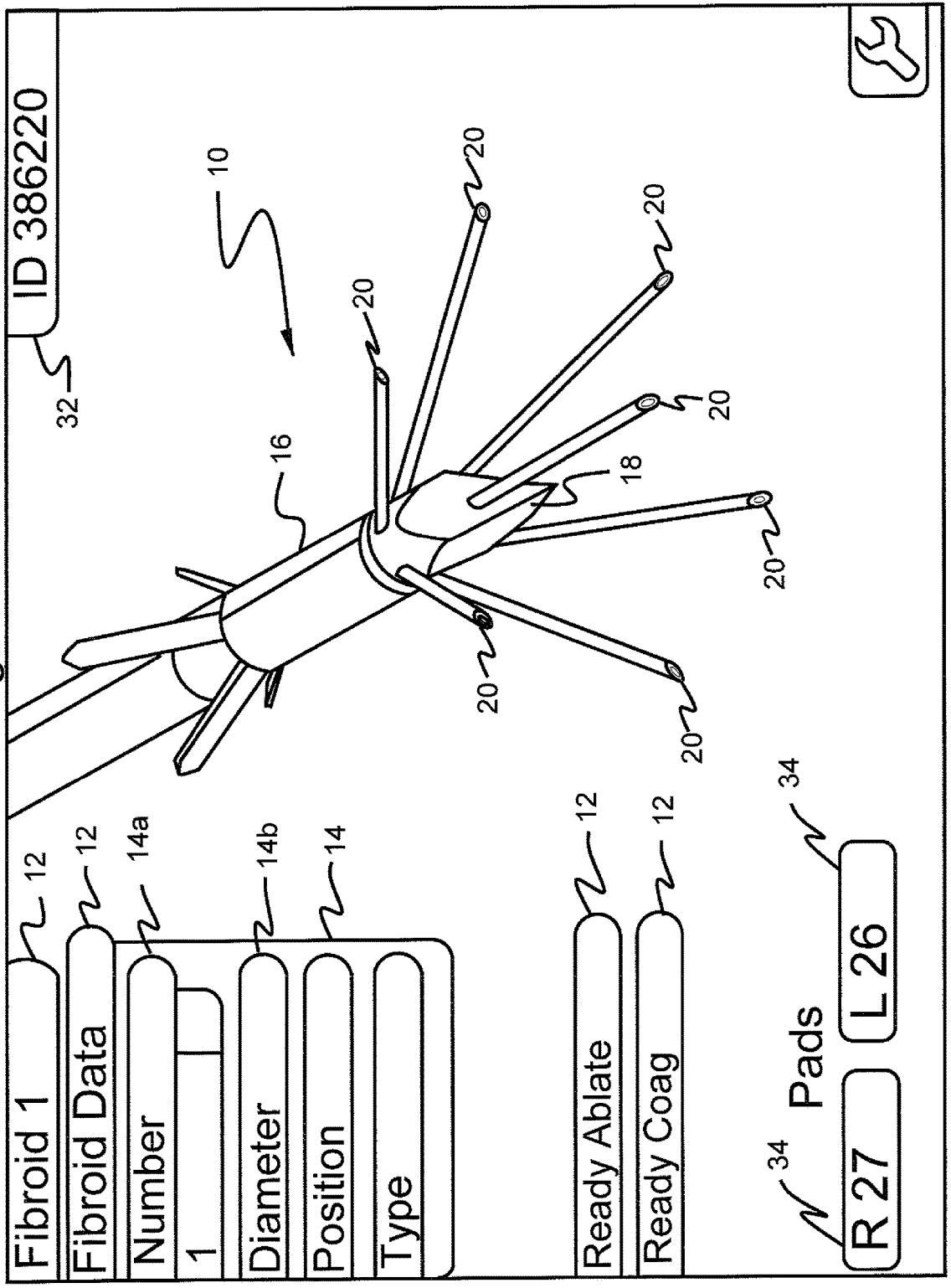
FIG. 2 shows the graphical user interface screen in which the menu "fibroid data" is selected to show submenus "number", "diameter", "position" and "type", and in which "1" is selected as the number.
Figure 3:
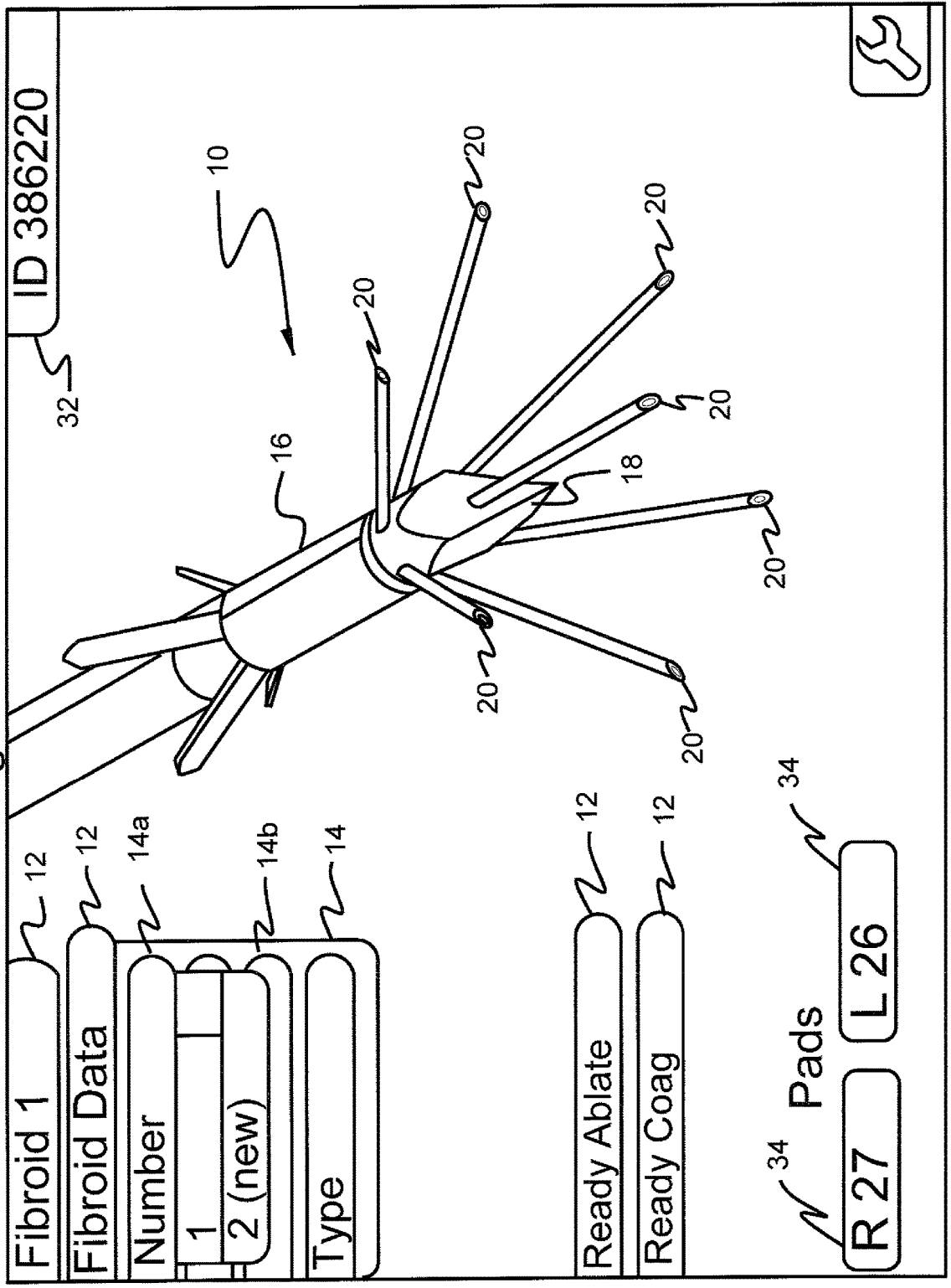
FIG. 3 shows the graphical user interface screen in which the menu "fibroid data" and the submenu "number" are selected, and in which "2" is selected as the number.
Figure 4:
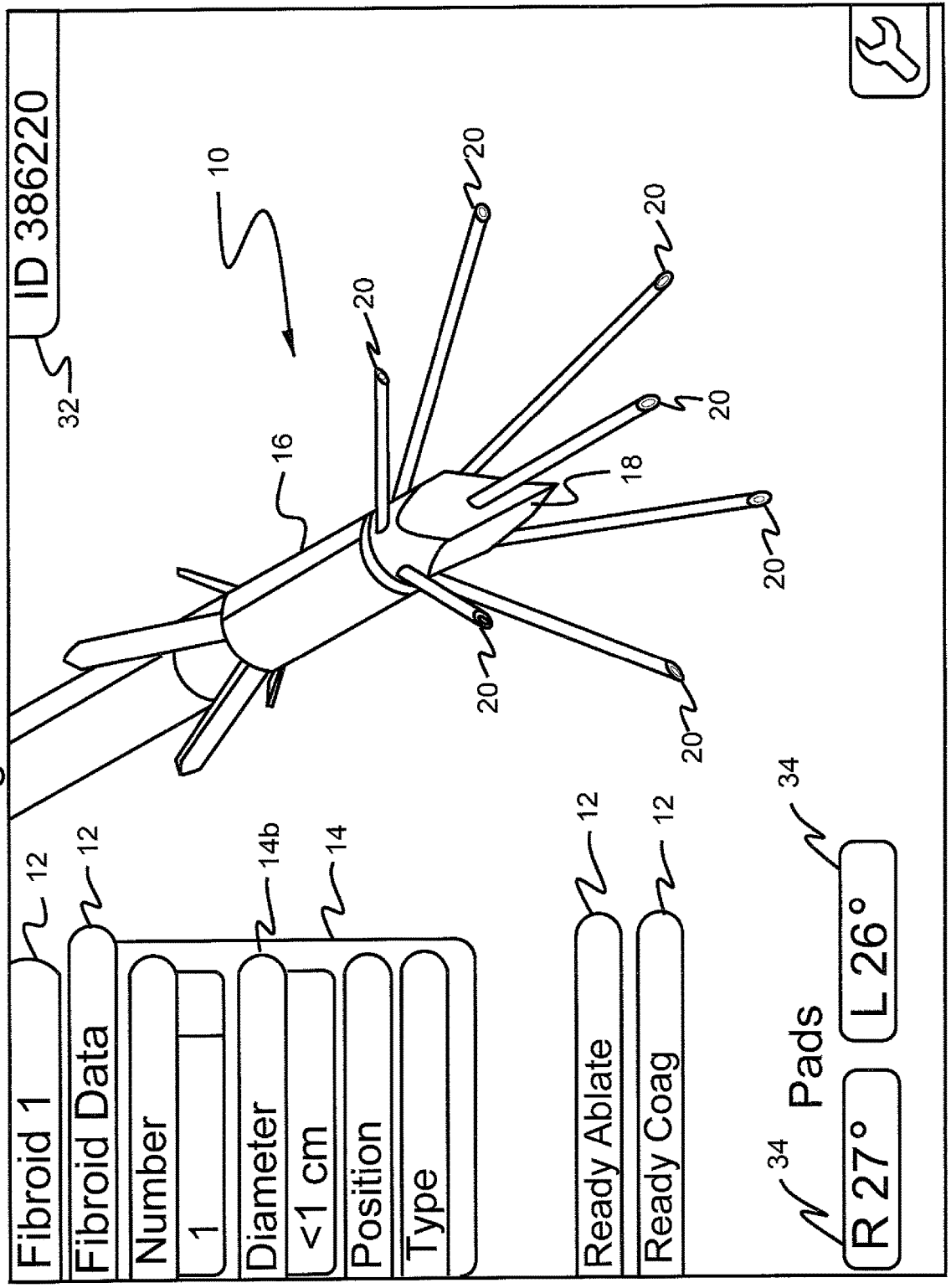
FIG. 4 shows the graphical user interface screen in which the menu "fibroid data" is selected, the submenu "diameter" is selected and a further submenu "<1 cm" is selected.
Figure 5:
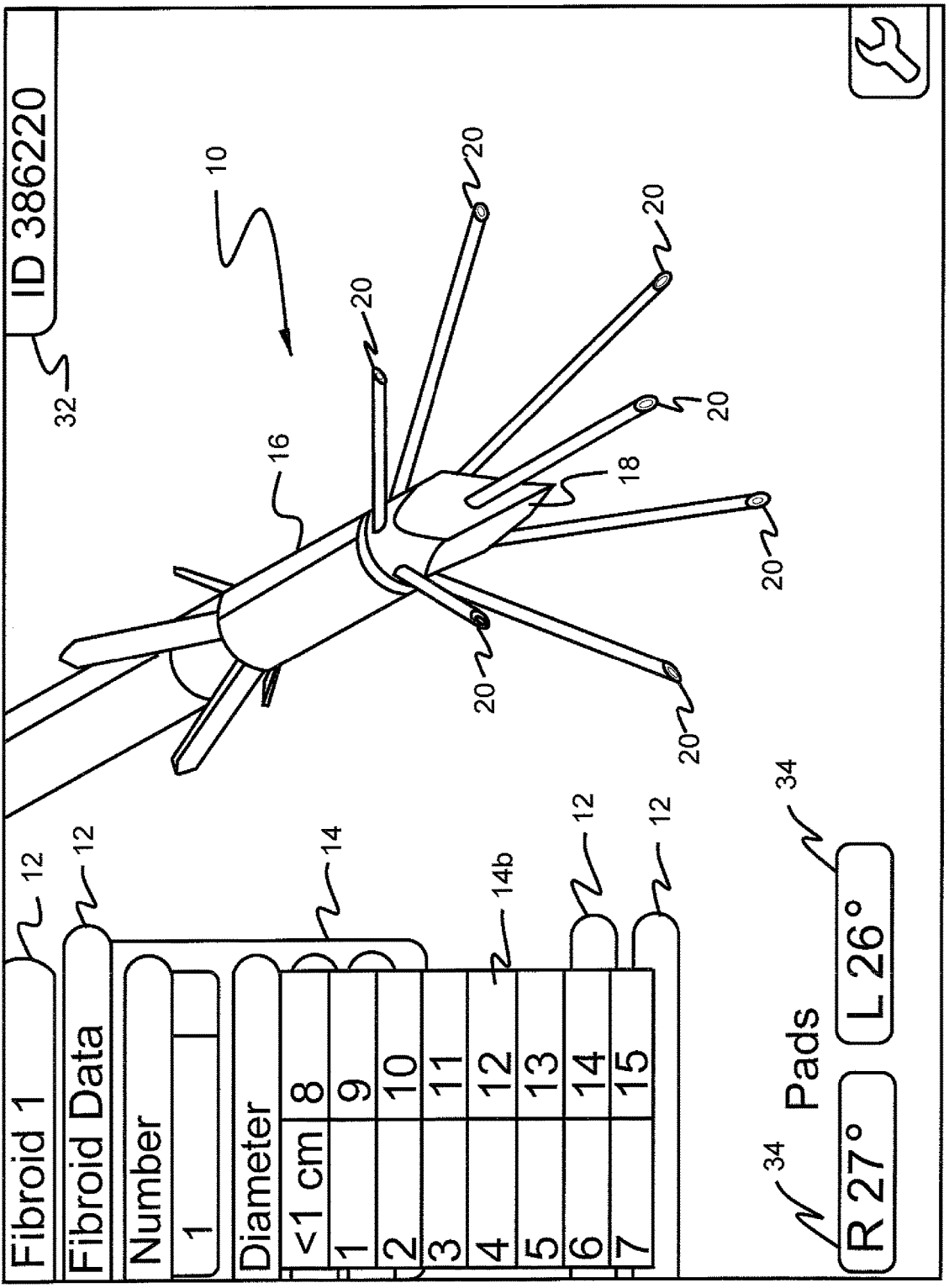
FIG. 5 shows the graphical user interface screen in which the menu "fibroid data" is selected, the submenu "diameter" is selected and further submenu choices are shown, which range from "<1 cm" to "15"
Figure 6:
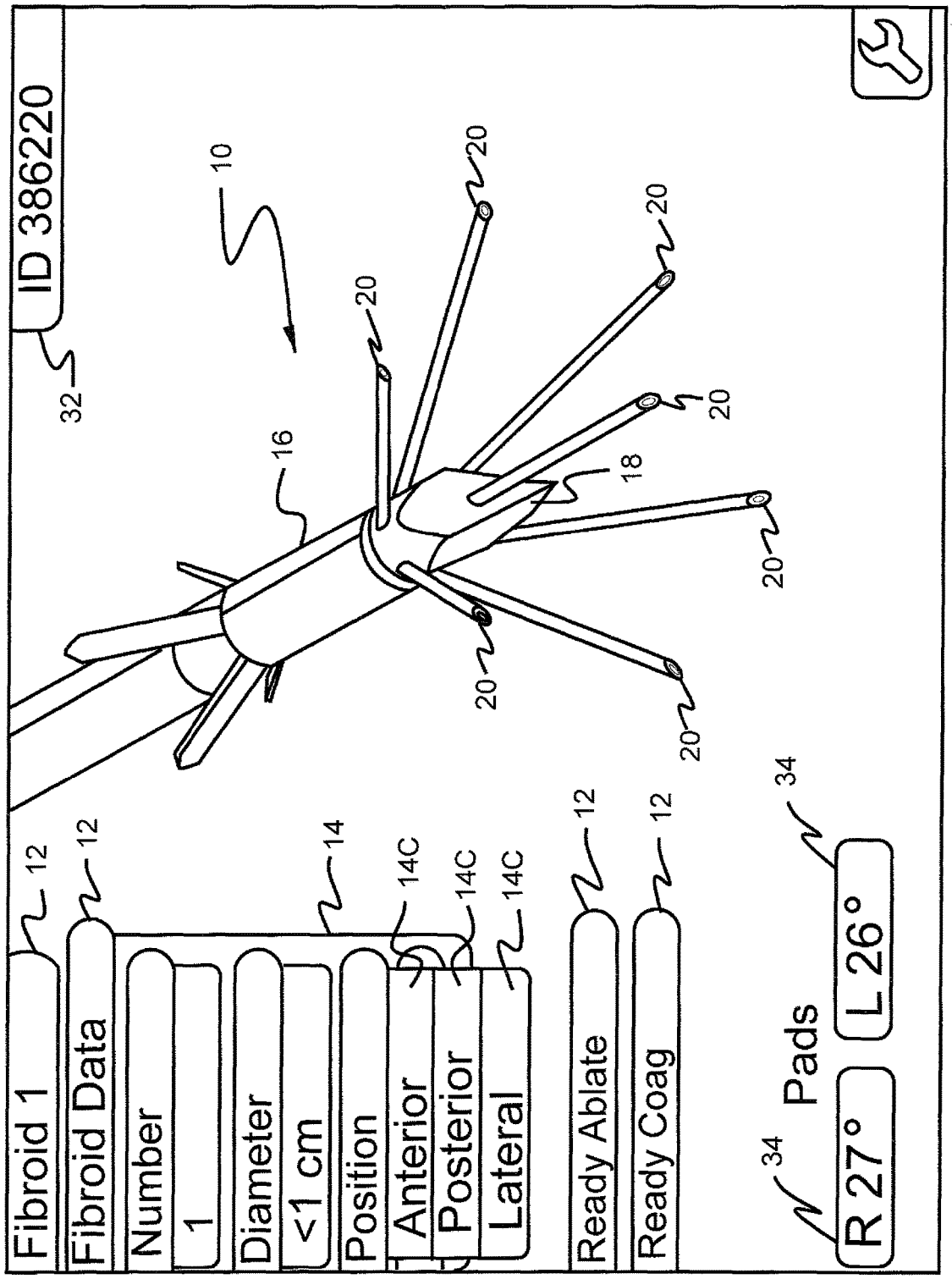
FIG. 6 shows the graphical user interface screen in which the menu "fibroid data" is selected, the submenu "position" is selected and further submenu choices "anterior", "posterior" and "lateral" are shown.

Referring to FIGS. 2-9, by scrolling to and selecting "Fibroid Data", a series of choices are presented in the form of a submenu 14. These choices allow for entering data regarding, in the illustrated example, a first uterine fibroid, namely "diameter", "position" and "type". Such information may be gathered by the surgeon based on, for example, ultrasound imaging and laparoscopic imaging. When submenu item 14a, "number", is scrolled to and selected, the practitioner can select the number associated with the fibroid, for example, "1" or "2" (FIGS. 2 and 3). When submenu item 14b, "diameter" is selected, as illustrated in FIG. 4, the size of the first fibroid is illustrated. Next, if the scroll button is depressed the system moves to the diameter indication "<1 cm". The diameter indication may be highlighted, indicating selection of the diameter indication. It is noted that indications of selection may be arrows, highlighting, or any suitable means. Depressing the select button when the diameter indication is highlighted results in presenting a submenu comprising a series of possible diameter values, as illustrated in FIG. 5. More particularly, this menu 14B displays choices ranging from <1 cm to 15 cm (FIG. 5) from which the practitioner can select, by scrolling to the proper size by repeatedly pressing the scrolling button and then pressing the select button when the proper size is highlighted. In this example, size "<1 cm" has been selected. Alternatively, or in addition, scrolling may be facilitated by grouping each function whereby pushing the scroll button down and keeping it down results in the machine automatically advancing through the sequence of choices.

When submenu item 14c "Position" is scrolled to and selected, further submenu 14C, which contains displays of "Anterior", "Posterior" and "Lateral" is displayed, presenting three choices from which the practitioner can select (FIG. 6) in order to make a record of the type of uterine fibroid. In this example, "Anterior" is selected.

Figure 7:
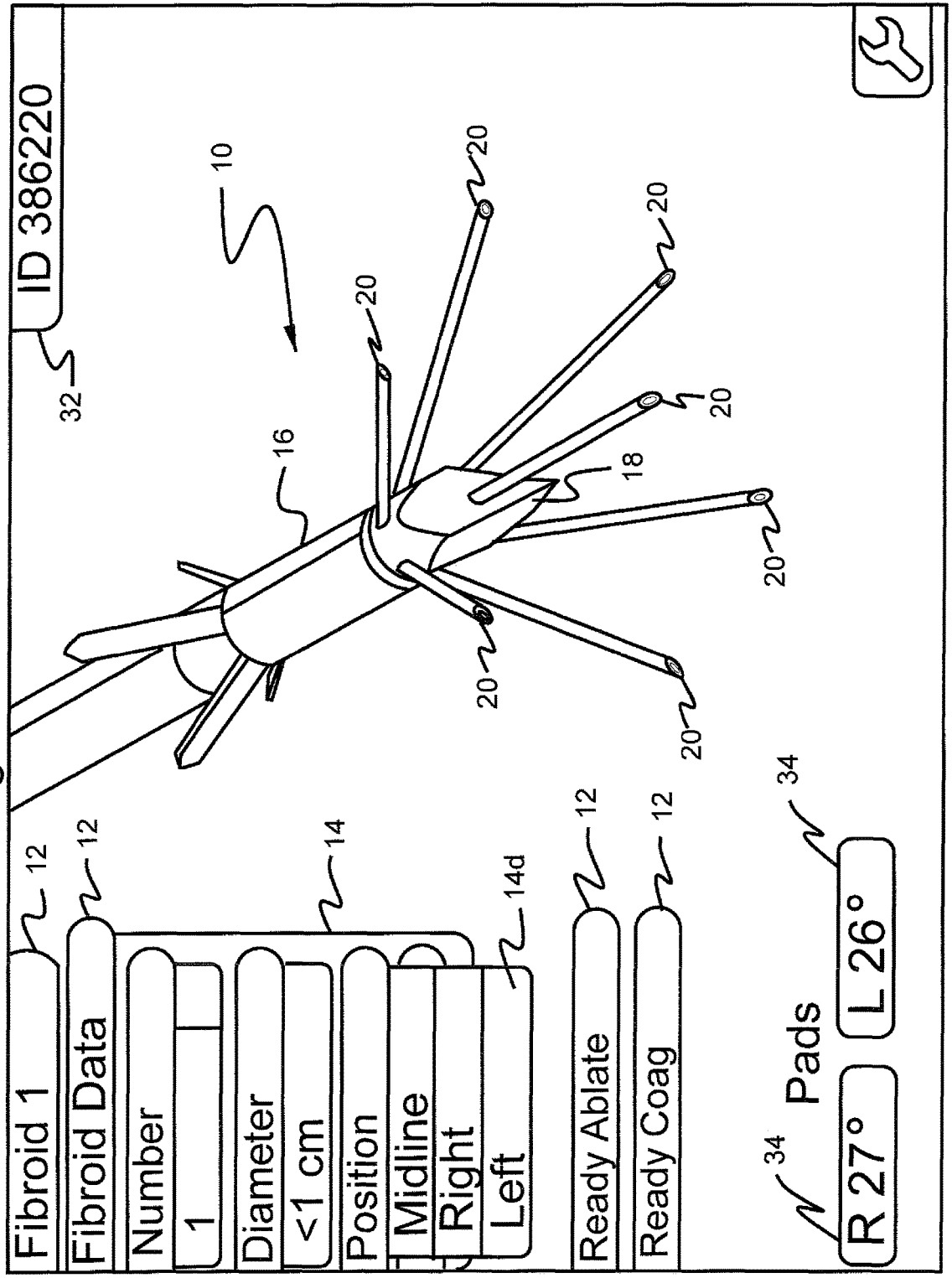
FIG. 7 shows the graphical user interface screen in which the menu "fibroid data" is selected, the submenu "position" is selected, and the further submenu choices "midline", "right" and "left" are shown.
Figure 8:
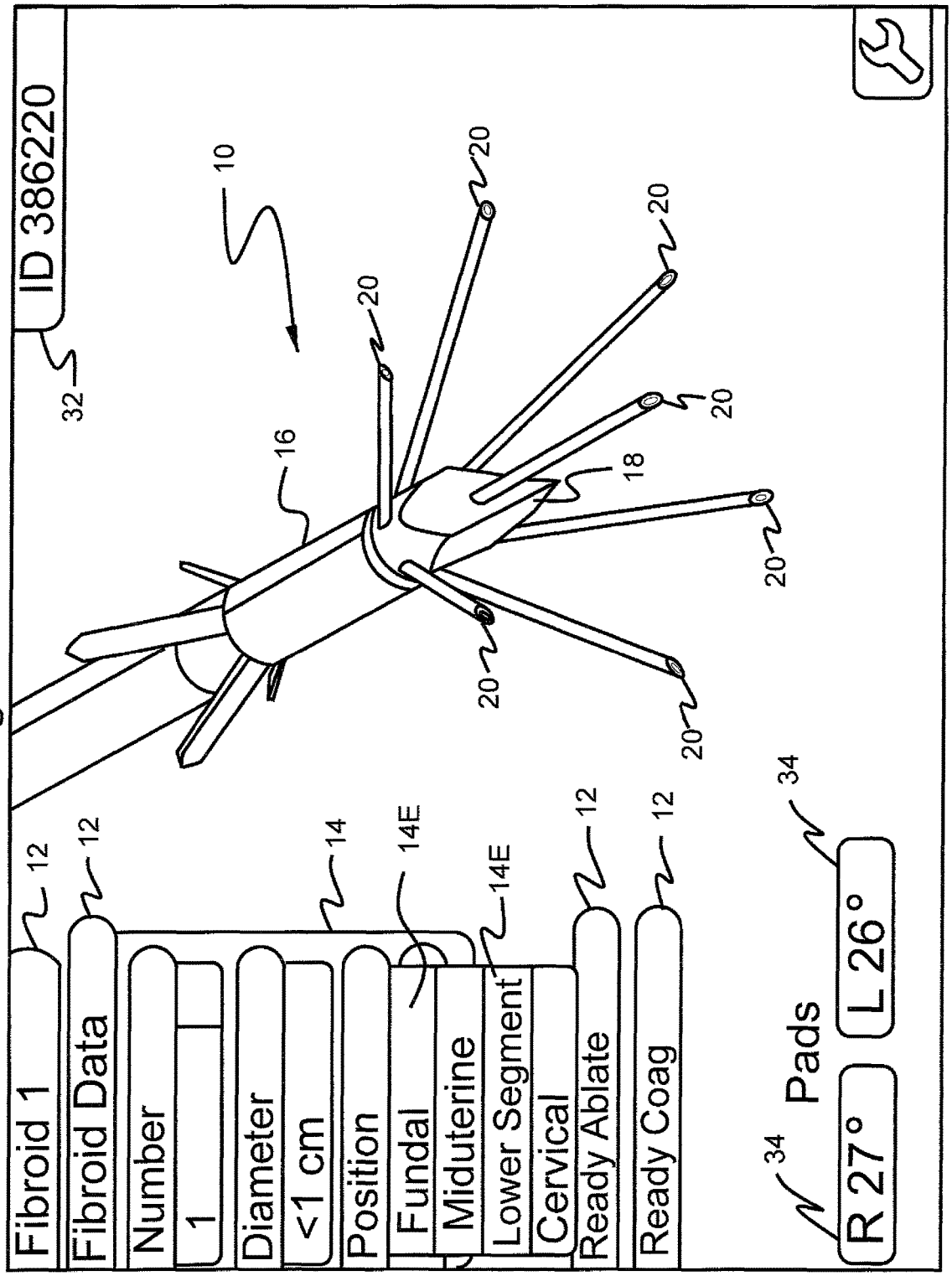
FIG. 8 shows the graphical user interface screen in which the menu "fibroid data" is selected, the submenu "position" is selected and the further submenu choices "fundal", "miduterine" and "lower segment" and "cervical" are shown.
Figure 9:
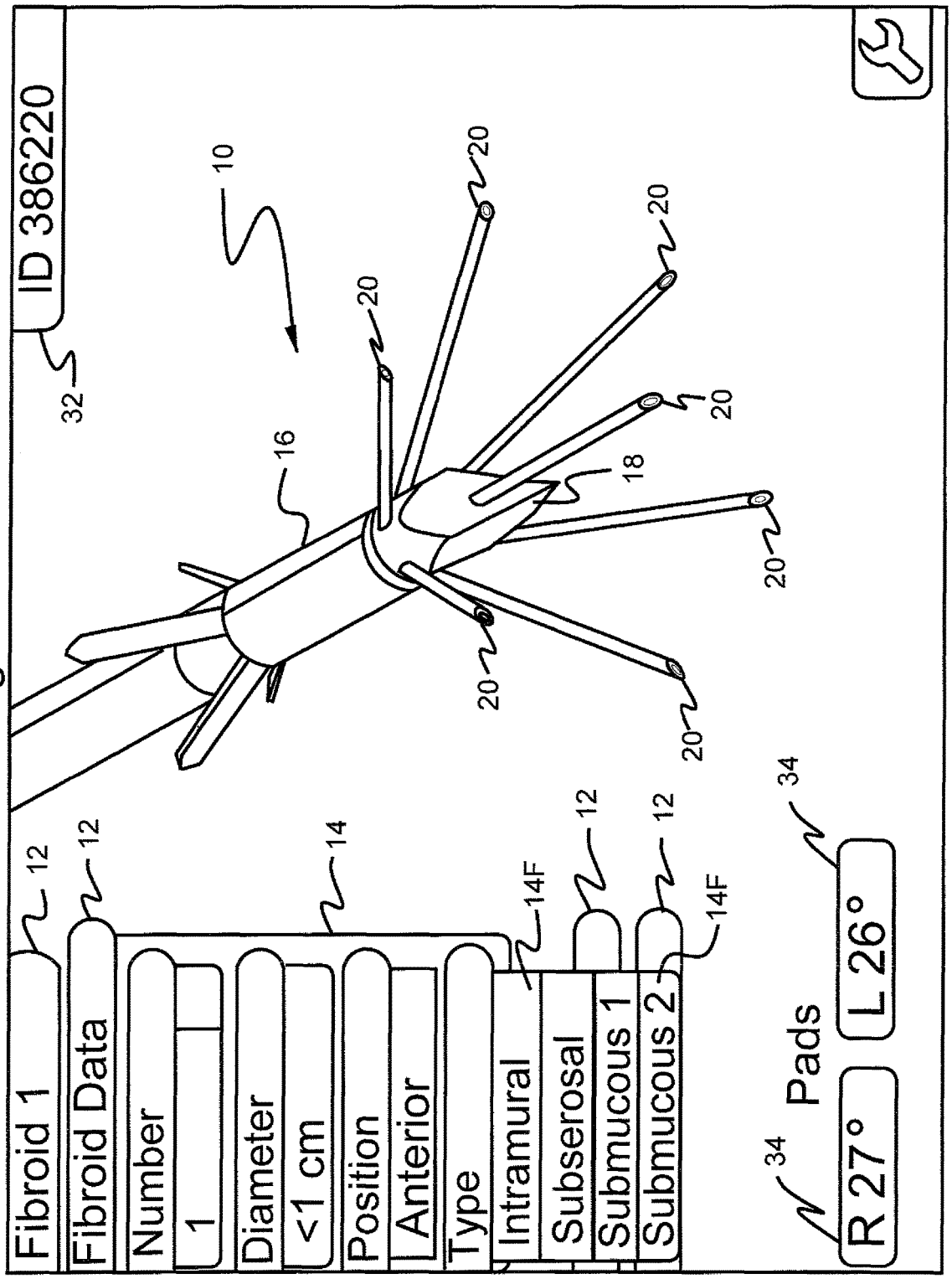
FIG. 9 shows the graphical user interface screen in which the menu "fibroid data" is selected, the submenu "diameter" is selected with the submenu "<1 cm" selected, the submenu "position" selected with the submenu "anterior" selected and the further submenu "type" showing the choices "intramural", "subserosal", "submucous 1" and "submucous 2"
Figure 10:
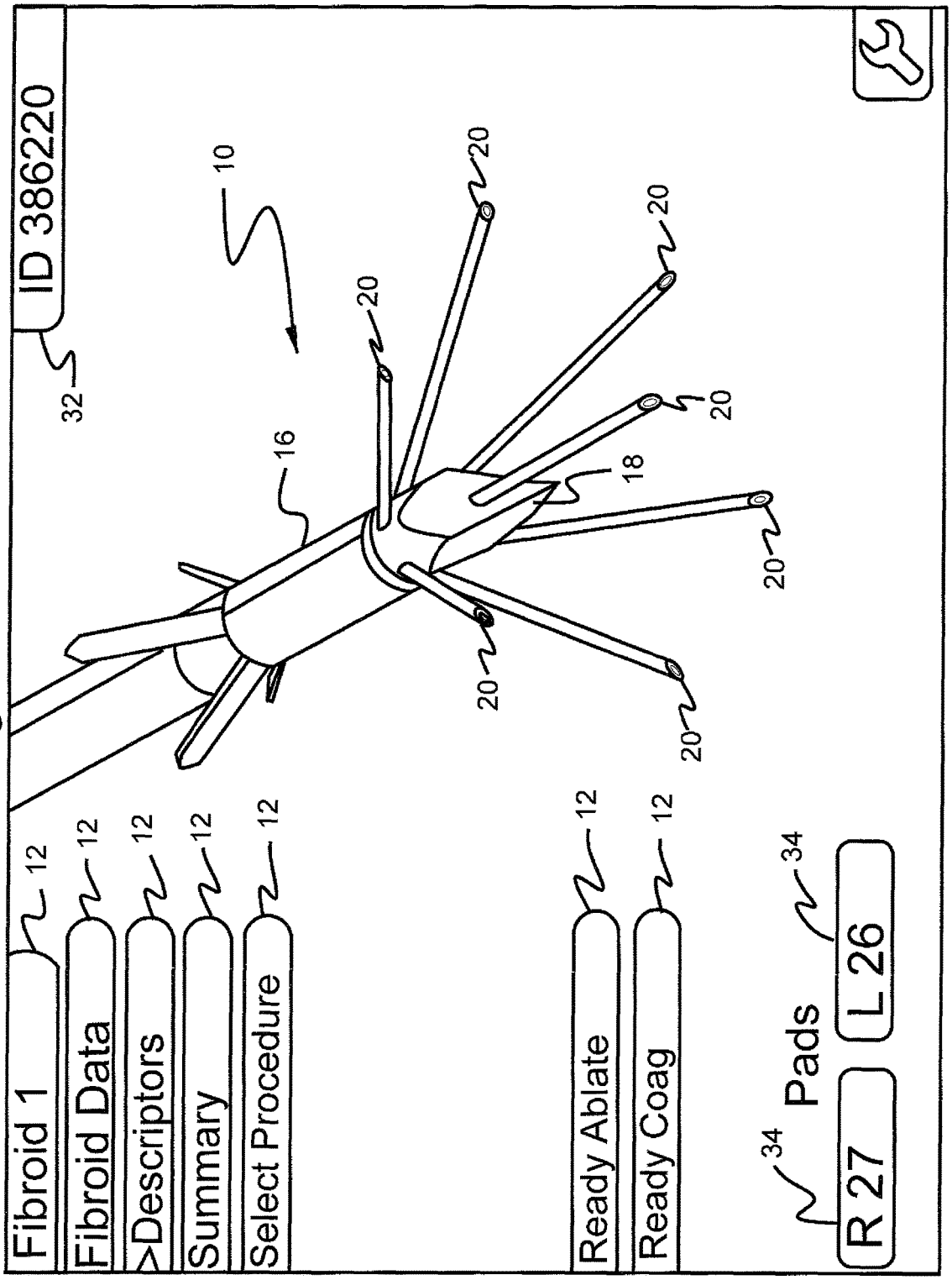
FIG. 10 shows the graphical user interface screen in which the navigational tool has scrolled to the menu choice "descriptors"
Figure 11:
FIG. 11 shows a table containing exemplary patient fibroid tumor data displayed on the graphical user interface when the menu "descriptors" is selected.
Figure 12:
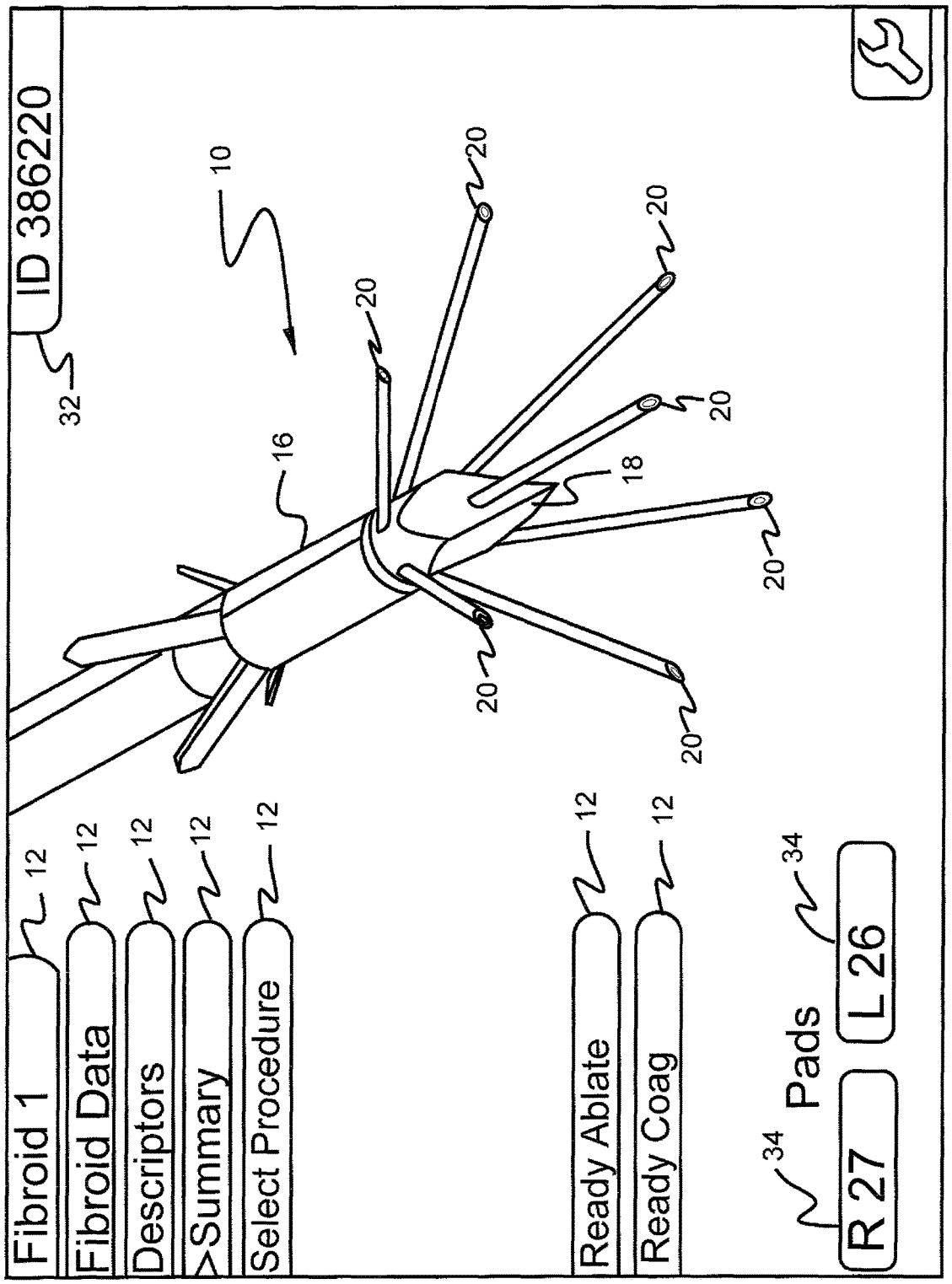
FIG. 12 shows the graphical user interface screen in which the navigational tool has scrolled to the menu choice "summary"
Figure 13:
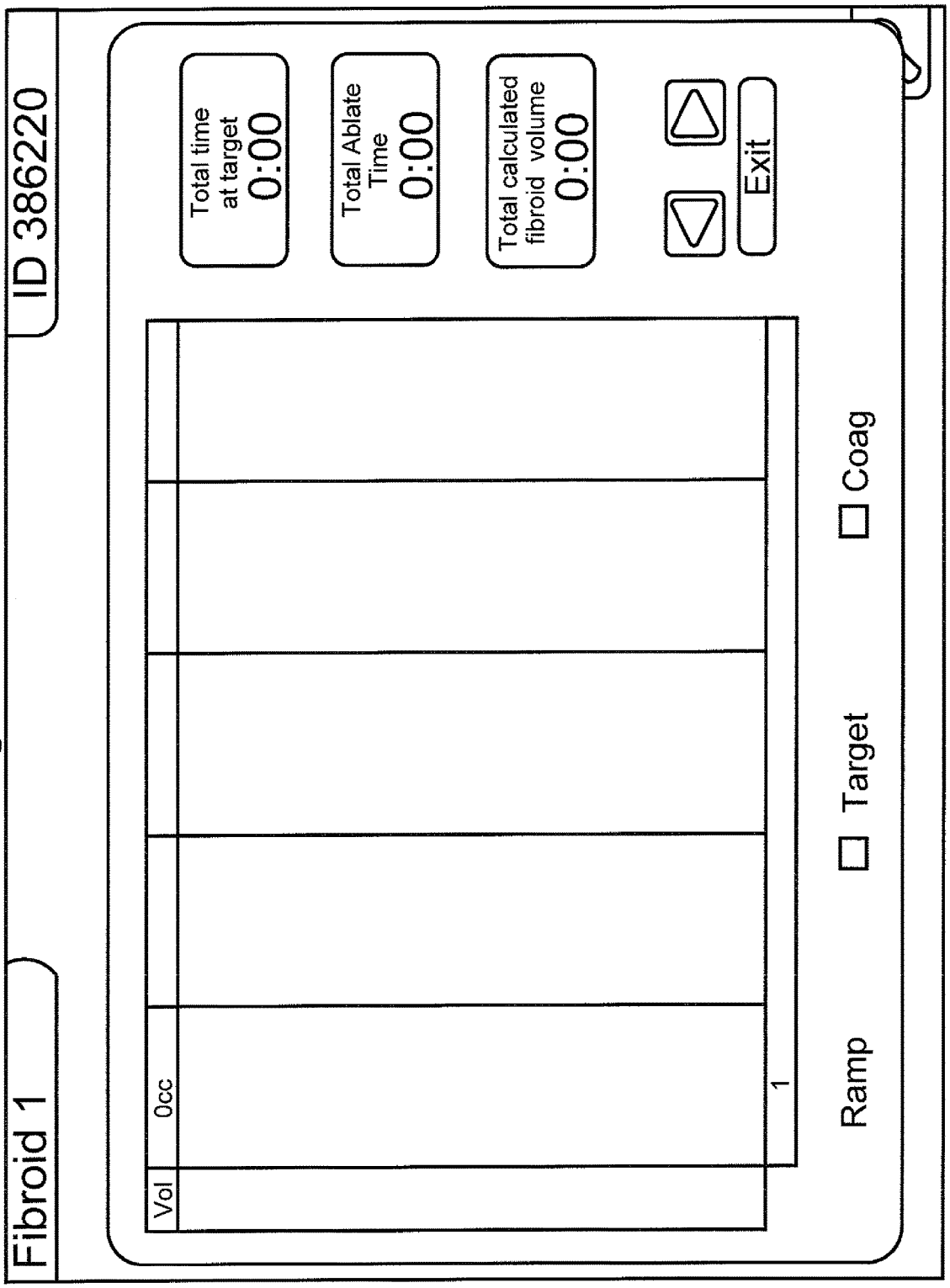
FIG. 13 shows a graphical compilation of exemplary patient fibroid tumor ablation data displayed on the graphical user interface when the menu "summary" is selected.

Upon making a selection from one of the items of submenu items 14B, a still further submenu of items 14D is produced, giving menu choices "Midline", "Right" and "Left", to which the practitioner can scroll and select (FIG. 7). In this example, "Midline" is selected. Upon making a selection from one of these submenu items 14D, still further submenu items 14E indicating "Fundal", "Miduterine", "Lower Segment" and "Cervical" are displayed, to which the practitioner can scroll and select (FIG. 8). In this example, "Fundal" is selected. Upon making a selection from one of these submenu items 14E, a still further submenu of items 14F "Intramural", "Subserosal", "Submucous 1" and "Submucous 2" are displayed, to which the practitioner can scroll and select (FIG. 9). In this example, "Intramural" is selected.

Referring to FIGS. 10-13, scrolling to menu 12 "Descriptors" (FIG. 10), and then pushing the select button opens a table (FIG. 11), in which all data selections detailed above that have been inputted in the "Fibroid Data" menu 14 are displayed on the GUI, and which allows input of the data for all fibroids. In this screen, the surgeon may scroll through the table items "Number", "Size", "Position", "Type", and "Exit". Like the other menu items in the inventive device, continuing to depress the scroll button will continue cycling through the menu selections. Accordingly, continuing to cycle through the menu items by pressing the scroll button will result in display of the table items "Number", "Size", "Position", "Type", "Exit", "Number", "Size", "Position", "Type", "Exit", "Number", "Size", "Position", "Type", "Exit", and so forth. Depressing the select button on any of these items will activate the arrow icon 17 and 19, and exit icon 21, which allows editing of the selected menu item.

Icons 17 and 19, when highlighted and selected by depression of the select button, actuate navigation through the various choices in opposite order. Icon 21, when highlighted by pressing of the scroll button and selected by depression of the scroll button, causes the system to exit the screen of FIG. 11 and go to the screen of FIG. 12.

Selecting the menu 12 "Summary" (FIG. 12) opens up a graphical display (FIG. 13), in which all data related to a particular fibroid tumor being ablated and associated patient identifier are displayed. This screen does not allow editing of the displayed information.

In general, in accordance with the preferred embodiment, items are scrolled to and selected by depression of the select button. However, in principle, resting the cursor for a particular length of time (for example, one second) can be set in the software to be the equivalent of a select, and this can be reversed by pushing the select button.

Figure 14:
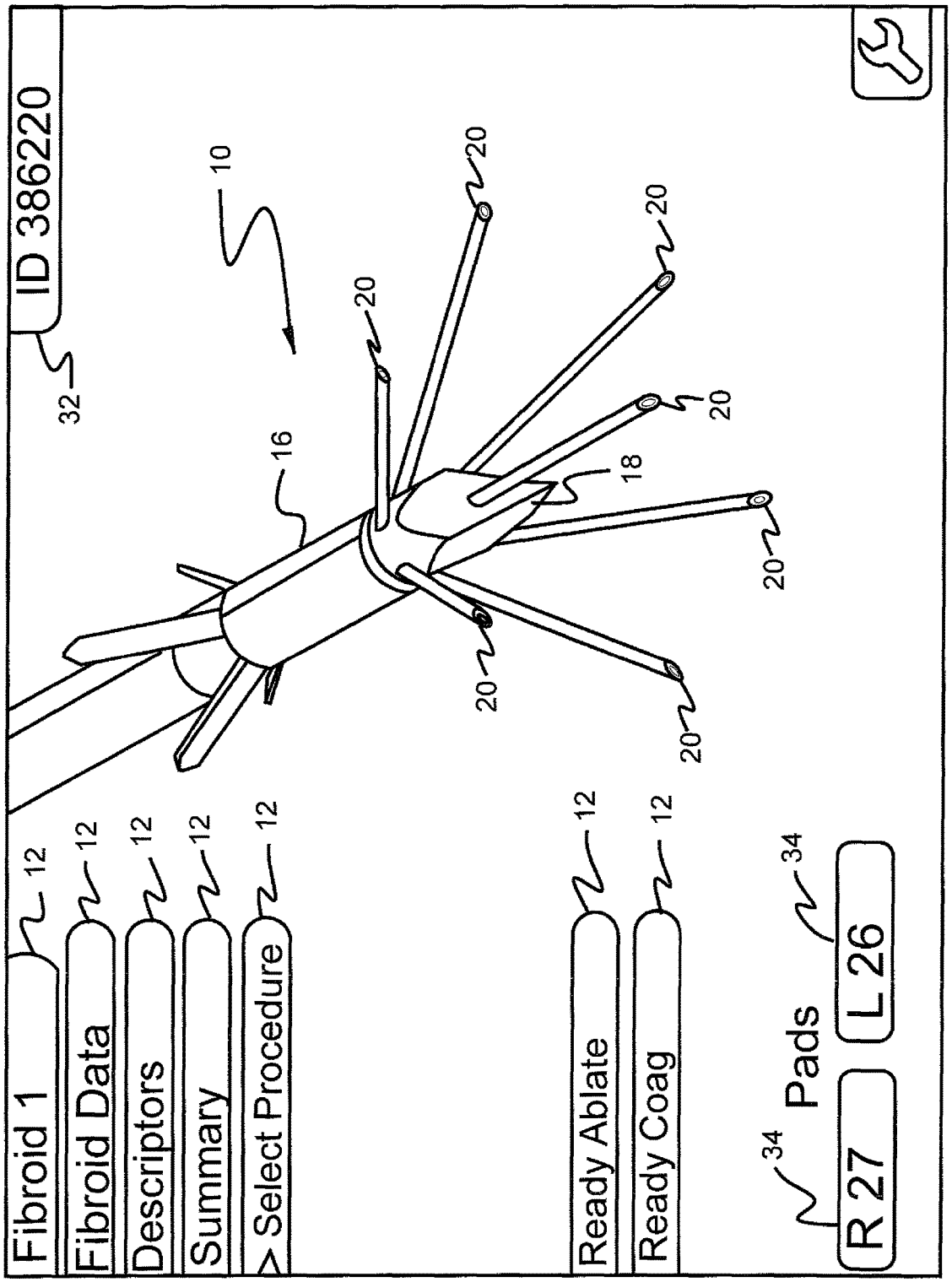
FIG. 14 shows the graphical user interface screen in which the navigational tool has scrolled to the menu choice "select procedure"

Referring to FIG. 14, the menu 12 choice "select procedure" is scrolled to by the practitioner to perform a surgical procedure of ablating a fibroid tumor. The practitioner can choose to bypass the "fibroid data", "descriptors" and "summary" menus 12 and scroll directly to the "select procedure" menu 12.

Referring to FIGS. 15-18, by selecting the "select procedure" menu 12, a "control mode" submenu 14 is displayed for selecting a target temperature and a target power level for RF ablation energy to be sent to trocar 18 and each of seven stylets 20 (RF energy delivery electrodes in accordance with the preferred embodiment) of the ablation device 16. Stylets 20 are illustrated on the touch screen display, which is itself illustrated in, for example, FIGS. 15-18. Stylets 20 have an internal volume that contains a wire thermocouple transducer, which performs the function of measuring temperature of the target tissue during the procedure which allows control of the ablation operation and ensures that the target tissue will become necrotic.

Figure 15:
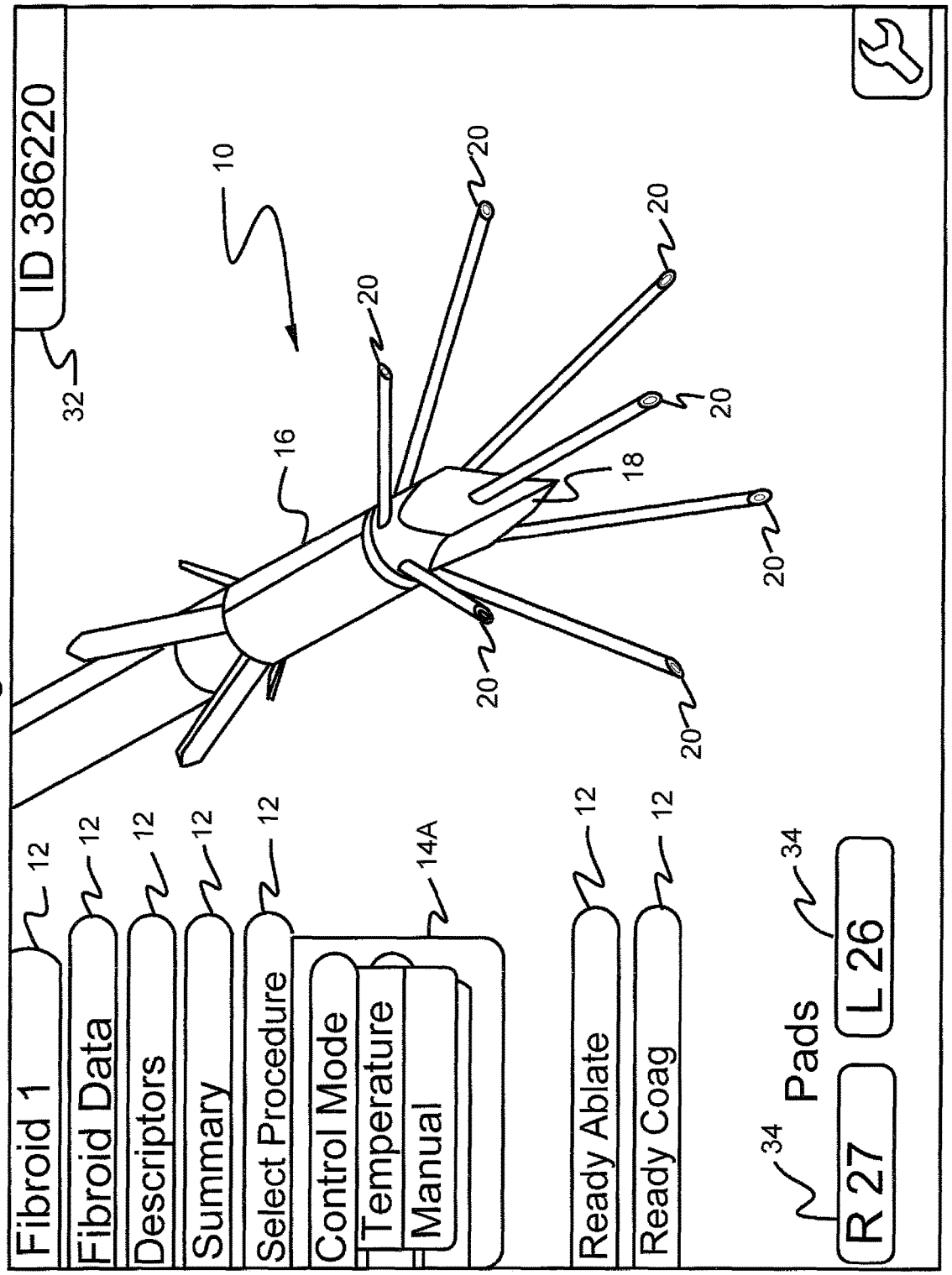
FIG. 15 shows the graphical user interface screen in which the menu "select procedure" is selected, the submenu "control mode" is selected, and the submenus "temperature" and "manual" are shown.
Figure 16:
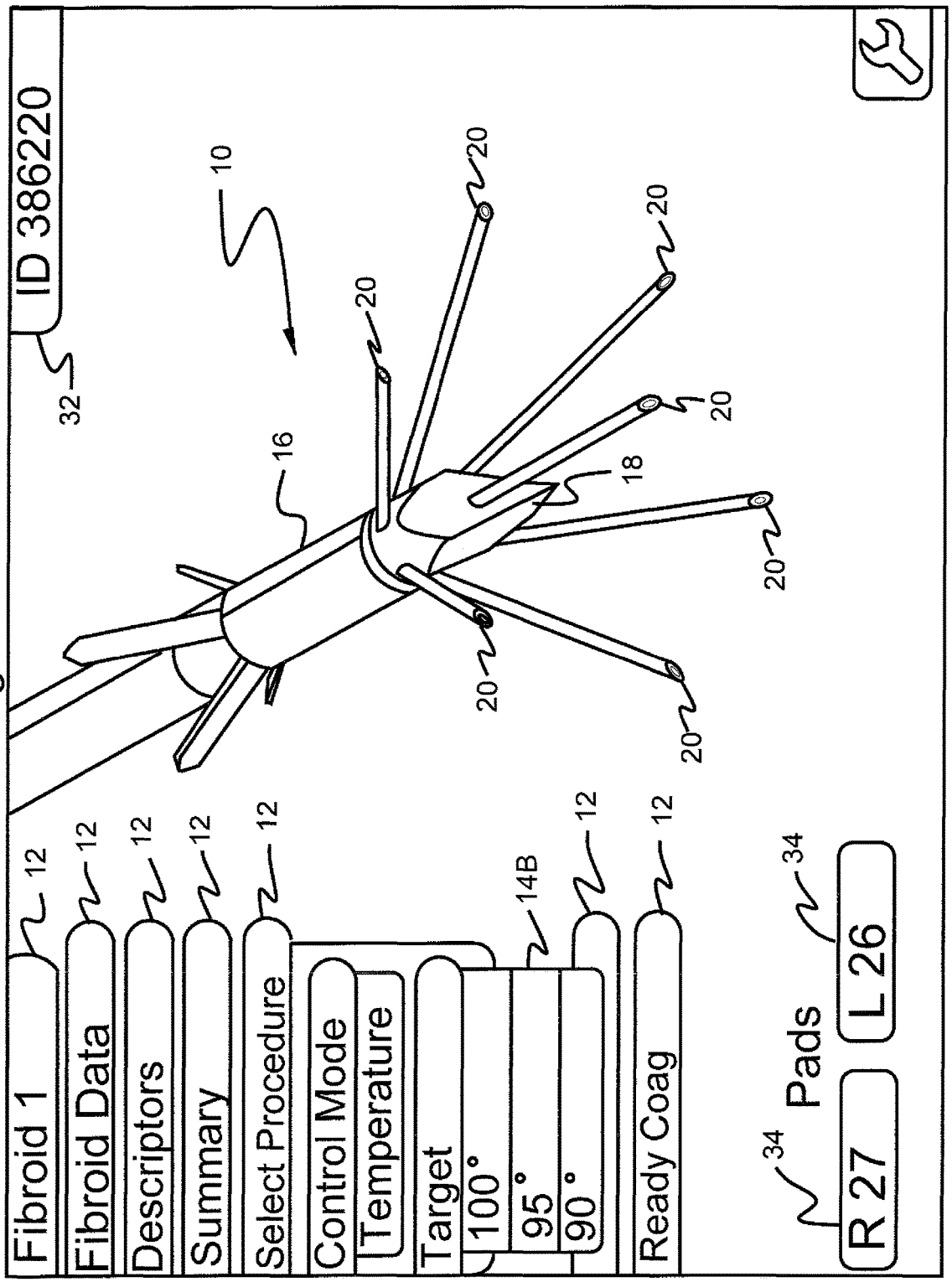
FIG. 16 shows the graphical user interface screen in which the menu "select procedure" is selected, the submenu "control mode" is selected, and the submenu "temperature" is shown with its submenus 90°, 95° and 100°.
Figure 17:
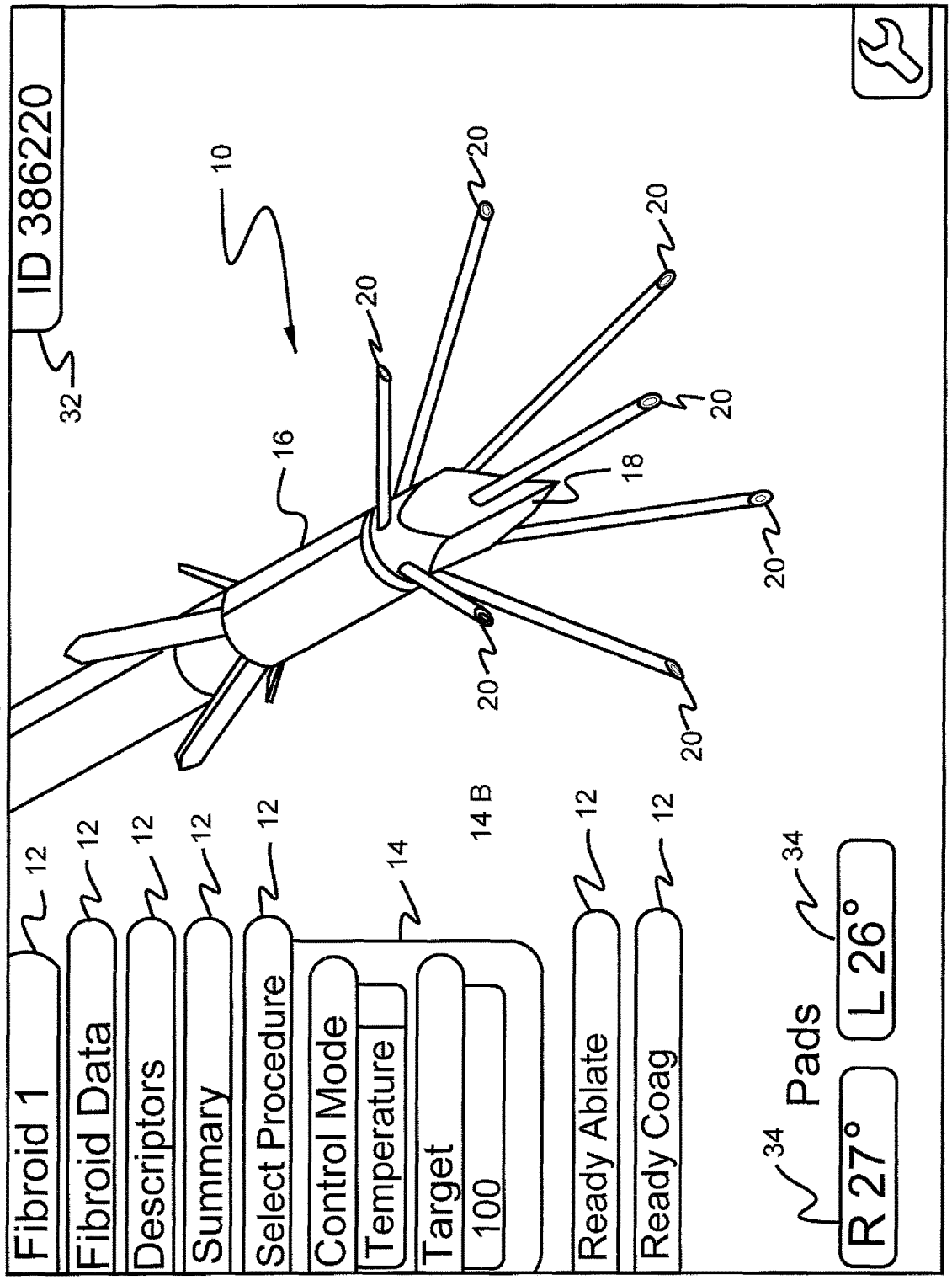
FIG. 17 shows the graphical user interface screen in which the menu "select procedure" is selected, the submenu" "control mode" is selected, a further submenu "temperature" is selected, and a temperature target of 100° is selected.
Figure 18:
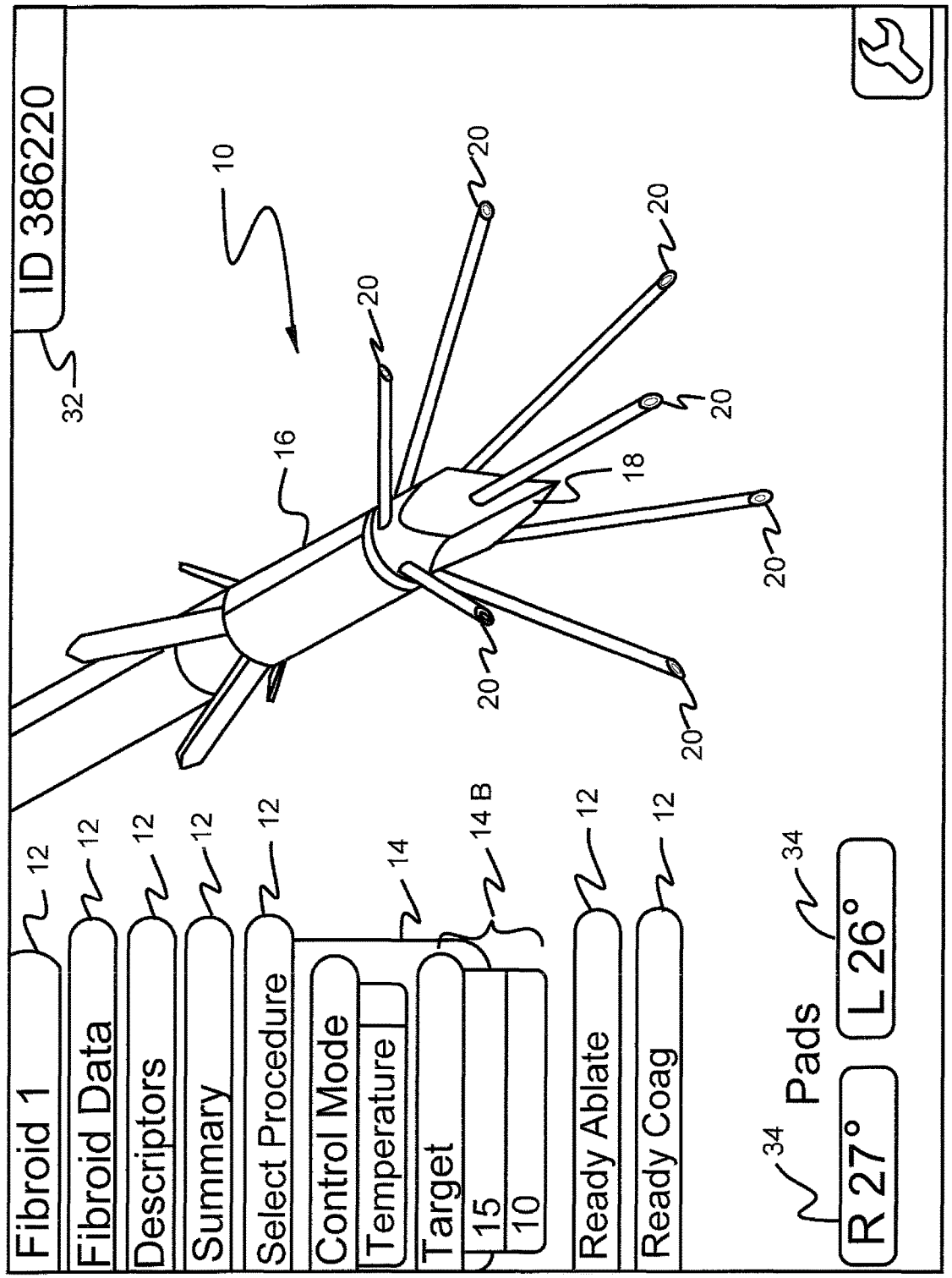
FIG. 18 shows the graphical user interface screen in which the menu "select procedure" is selected, the submenu" "manual" is selected, and the submenu target power levels of "15" and "10" are displayed.
Figure 19:
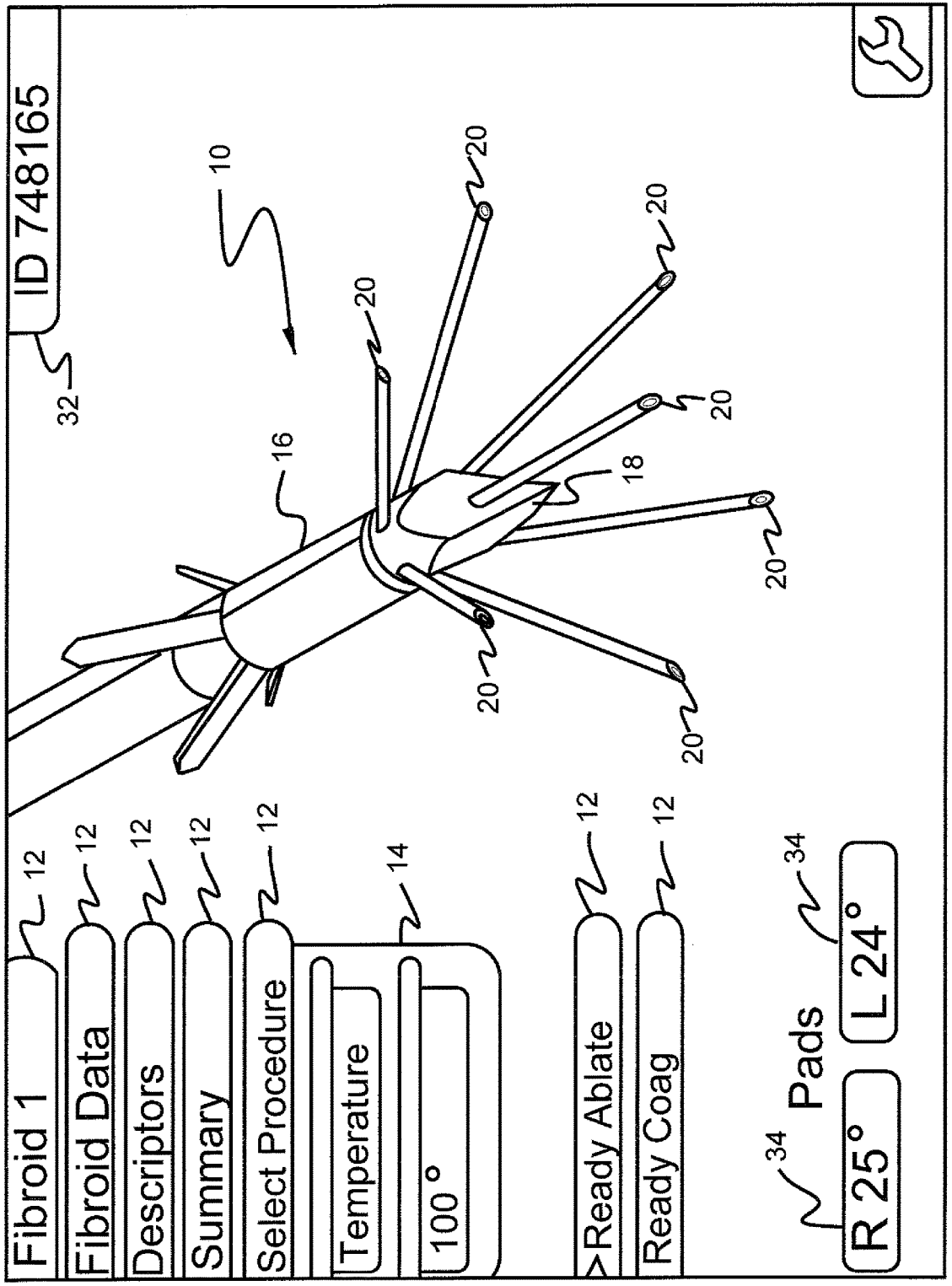
FIG. 19 shows the graphical user interface screen in which the menu "select procedure", the submenu "temperature" and 100° have been selected; and the navigational tool has scrolled to the menu choice "ready ablate"

When submenu 14 item "control mode" is scrolled to and selected, "temperature" and "manual" submenus 14A are displayed (FIG. 15). The practitioner may then select the target temperature by selecting submenu 14A item "temperature". A further submenu 14B "target" is displayed having three temperature choices: 100° C., 95° C. and 90° C. (FIG. 16), from which the practitioner can select a target temperature. FIG. 17 shows the display upon selection of 100° C. by the practitioner as the target temperature chosen for stylets 20 of the ablation device 16. In this mode the system controls the temperature to be at approximately the selected temperature, in the example 100 degrees C. by turning RF energy on and off, for as long as the foot pedal coupled to the RF generator is telling the system to stay on.

Alternatively, the surgeon may scroll to and select "Manual" from the menu as illustrated in the screen of FIG. 15. This brings up the screen of FIG. 18. The practitioner chooses the target power level of RF energy emitted from the seven stylets 20 by selecting the desired power from further submenu 14B, where "target" is displayed. A choice of two target power levels is presented, namely 15 watts and 10 watts (FIG. 18), from which the practitioner can select the target power level. In this mode the surgeon or other practitioner uses the foot pedal to "manually" turn the RF output on and off.

Figure 20:
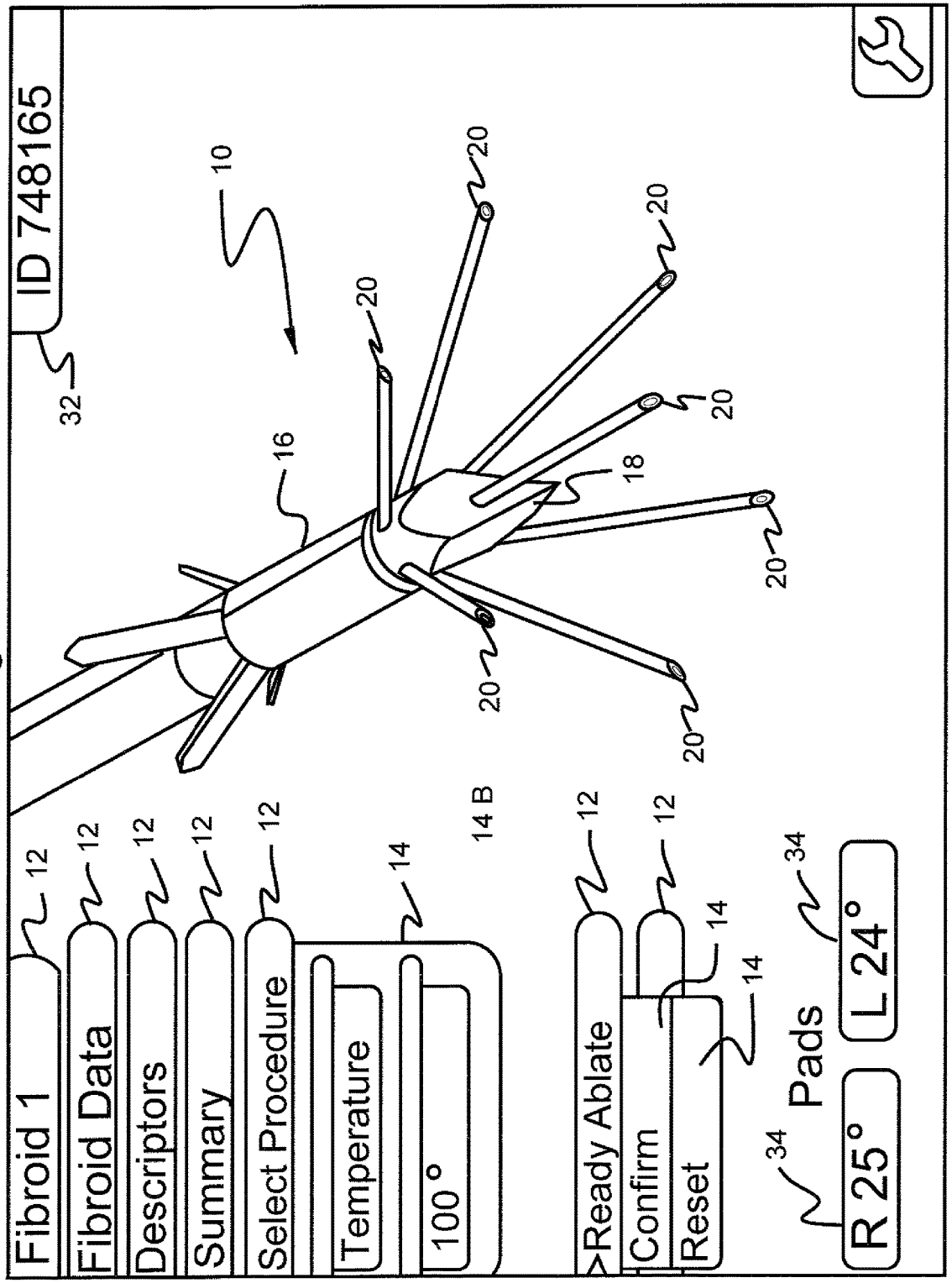
FIG. 20 shows the graphical user interface screen in which the menu "select procedure", the submenu "temperature" and 100° have been selected; and the menu "ready ablate" has been selected showing the submenu choices "confirm" and "reset;"
Figure 21:
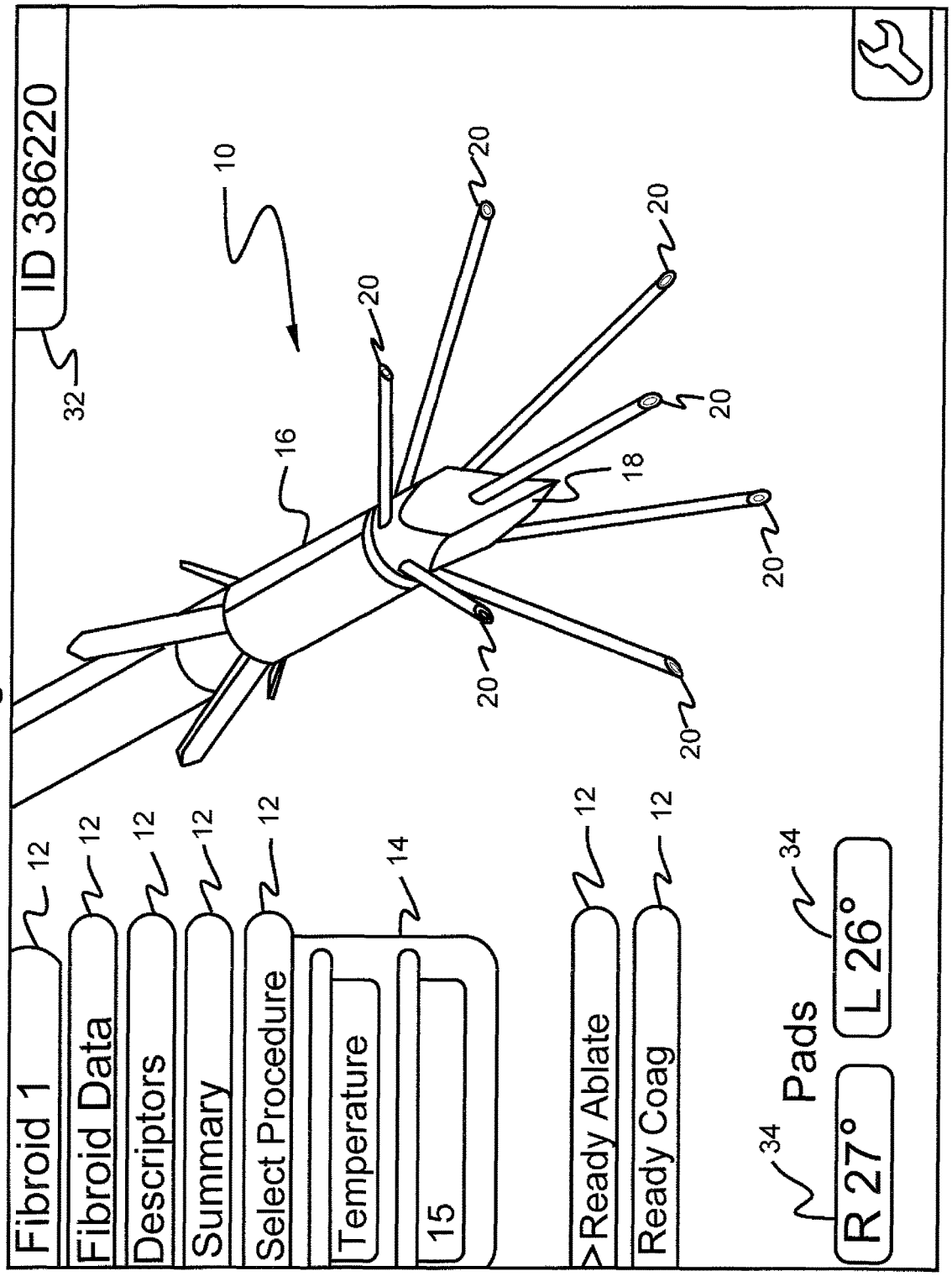
FIG. 21 shows the graphical user interface screen in which the menu "select procedure", the submenu "manual" and power level target "15" have been selected; and the navigational tool has scrolled to the menu choice "ready ablate"
Figure 22:
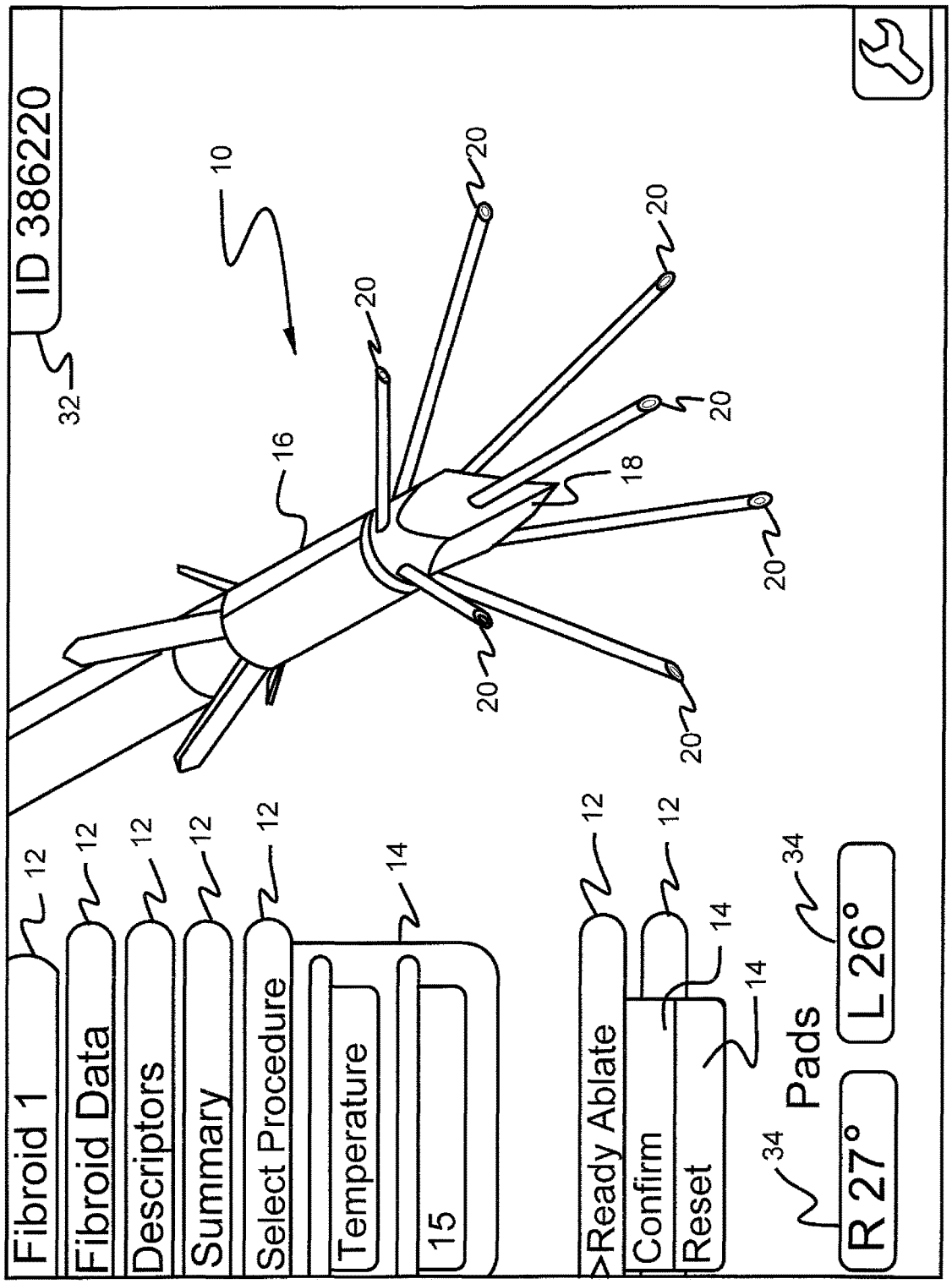
FIG. 22 shows the graphical user interface screen in which the menu "select procedure", the submenu "manual" and power level target "15" have been selected; and the menu "ready ablate" has been selected showing the submenu choices "confirm" and "reset;"
Figure 23:
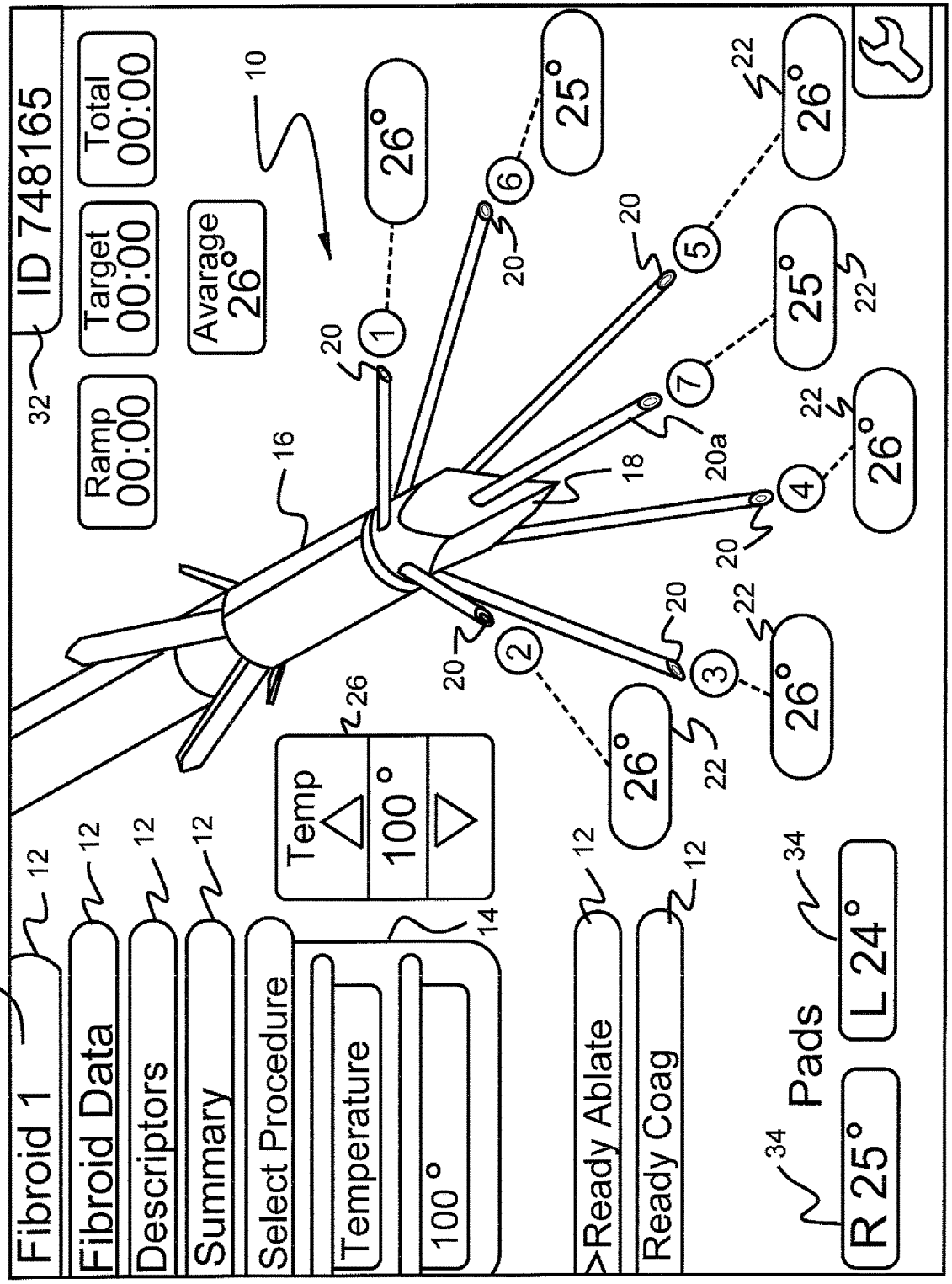
FIG. 23 shows the graphical user interface screen in which the menu "select procedure", the submenu "temperature" and the temperature of "100°" have been selected at the start of ablation of the fibroid tumor; also shown is the average temperature and the temperature in tissue adjacent to each of the stylets of the ablation device as well as the temperature in right and left pads placed on a patient's legs.

Returning back to the case where the surgeon has elected to have the system maintain a target temperature automatically by turning the RF energy on and off in response to temperature measurements by the transducers in the stylets, and referring to FIGS. 19-22, the practitioner starts ablation of the fibroid tumor by scrolling to and selecting the menu 12 "ready ablate" (FIGS. 19 and 21), which displays two submenu 14 items, namely "confirm" and "reset" (FIGS. 20 and 22). "Reset" brings the system back to the screen of FIG. 15, for selection between temperature and manual control.

In accordance with a preferred embodiment, and referring to FIGS. 23-27, after selecting the target temperature 26, the menu 12 "ready ablate", and the submenu 14 item "confirm", a new screen (FIG. 23) is displayed on the GUI 10 which shows the ablation device 16 and various parameters of the surgical field. The practitioner can scroll through this new screen and make adjustments to the target temperature 26 (for example in 1 degree C. increments) by selecting the select button on the navigational tool. Likewise, if manual control has been selected, adjustments to the selected power level 30 can be made, for example, in one watt increments. The practitioner can return to the main menu by scrolling through the menu 12 choices and selecting any menu 12 item other than "ready ablate" or "ready coag" in, for example, the screen of FIG. 23.

In the preferred embodiment, the number assigned to the fibroid undergoing ablation, i.e., "fibroid number" indication 36, is displayed. The number assigned to the patient, i.e., patient "ID" number 32, is also displayed. The target temperature indicator 26 set by the practitioner is displayed. The target temperature 26 may be adjusted up or down by the practitioner during the surgical procedure. Stylet temperature readings 22 for each of the seven stylets 20 are displayed. Average temperature display 24 which reads the average temperature in the tissue adjacent all of the stylets 20 is displayed. The practitioner may choose to not use certain stylets 20 as part of the calculation of the average temperature 24. For example, the highest and lowest measurement readings may be removed from the calculation. Typically, the central stylet (stylet 20a) is not used in the calculation of the average temperature 24 as this stylet tends to be mechanically deflected in the tissue mass in a difficult to predict manner. The temperature of the right and left pads is displayed by indicator 34. Such pads contain three thermocouples. Display 34 indicates the highest temperature on each pad, and is displayed for the right and left pads, displayed in the indicators labeled "R" and "L" on GUI 10. The time elapsed from the start of the application of RF ablation energy is displayed as "ramp" time on display 27 on GUI 10. The time elapsed once the temperature of the tissue mass has reached the preset target temperature displayed on indicator 26 (which is the average temperature displayed in indicator 24 in tissue adjacent to each of the seven stylets 20 selected for this calculation) is displayed as "target" time on indicator 28 on GUI 10. The target time (that is time at the targeted temperature) displayed on indicator 28 at this preset target temperature shown on indicator 26 can range from about 10 seconds to about 20 minutes depending on the size of the tissue mass being ablated and deployment of the ablation device. The total time elapsed from the start of ablation to the end of ablation is displayed as "total" time indicated on display 29 on GUI 10.

Figure 24:
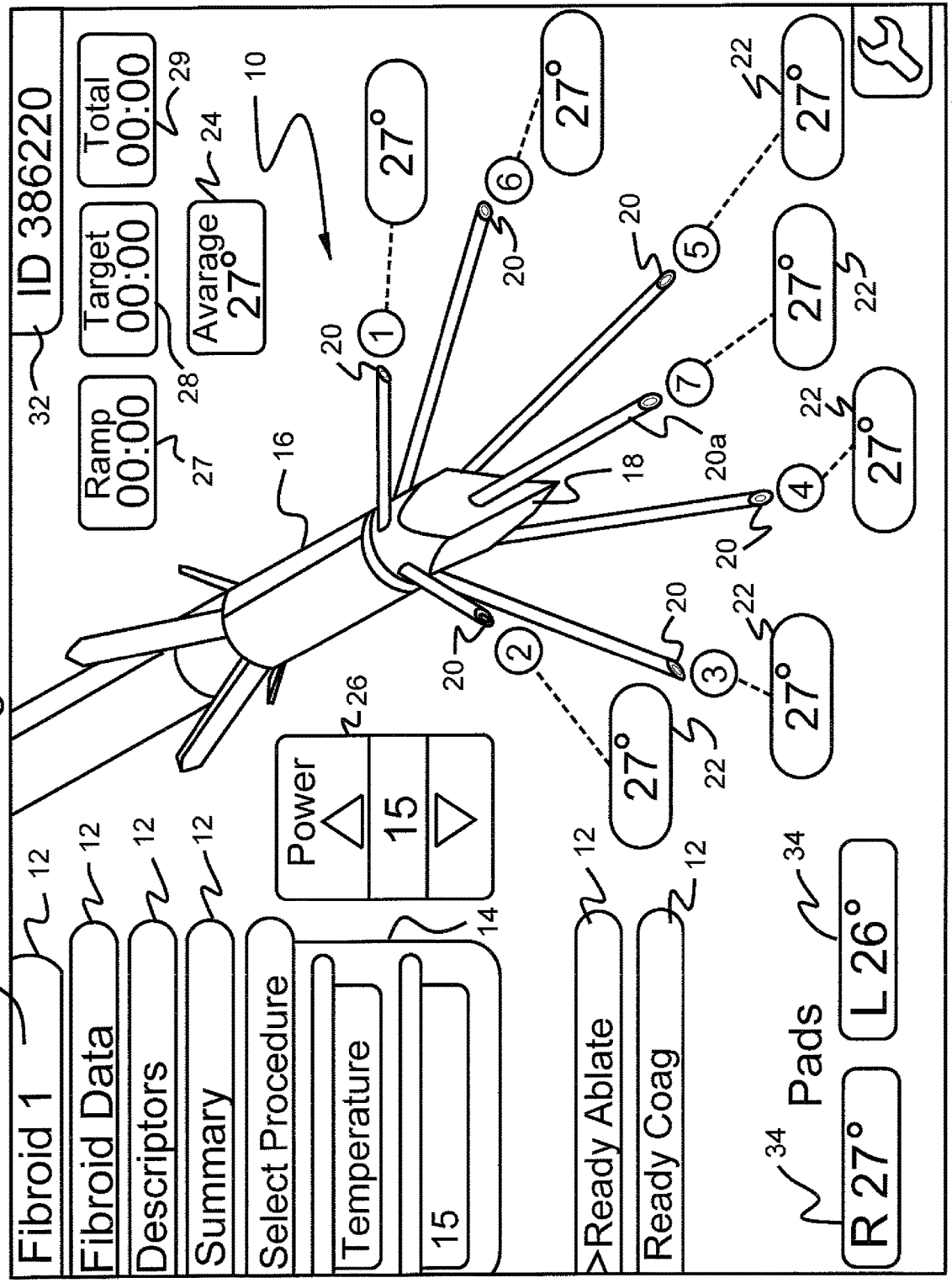
FIG. 24 shows the graphical user interface screen in which the menu "select procedure", the submenu "manual" and the target power level of "15" have been selected at the start of ablation of the fibroid tumor; also shown is the average temperature and the temperature in tissue adjacent to each of the stylets of the ablation device, the power level submenu as well as the temperature in the right and left pads placed on a patient's legs.

Referring to FIG. 24, operation in the "manual" mode is similar. After selecting the target power level indicated on display 30, the menu 12 item "ready ablate", and the submenu 14 "confirm" (FIG. 22), GUI 10 displays the same parameters as described hereinabove with the exception that the target power level (indicated on display 30) chosen by the practitioner. In the example shown in FIG. 24, this is 15 watts. The target power level indicated in display 30 may be adjusted up or down by the practitioner during the surgical procedure. The target power level indicated in display 30 represents the amount of RF energy emitted from the stylets and trocar of the ablation device at a standard frequency of 460 KHz.

Figure 25:
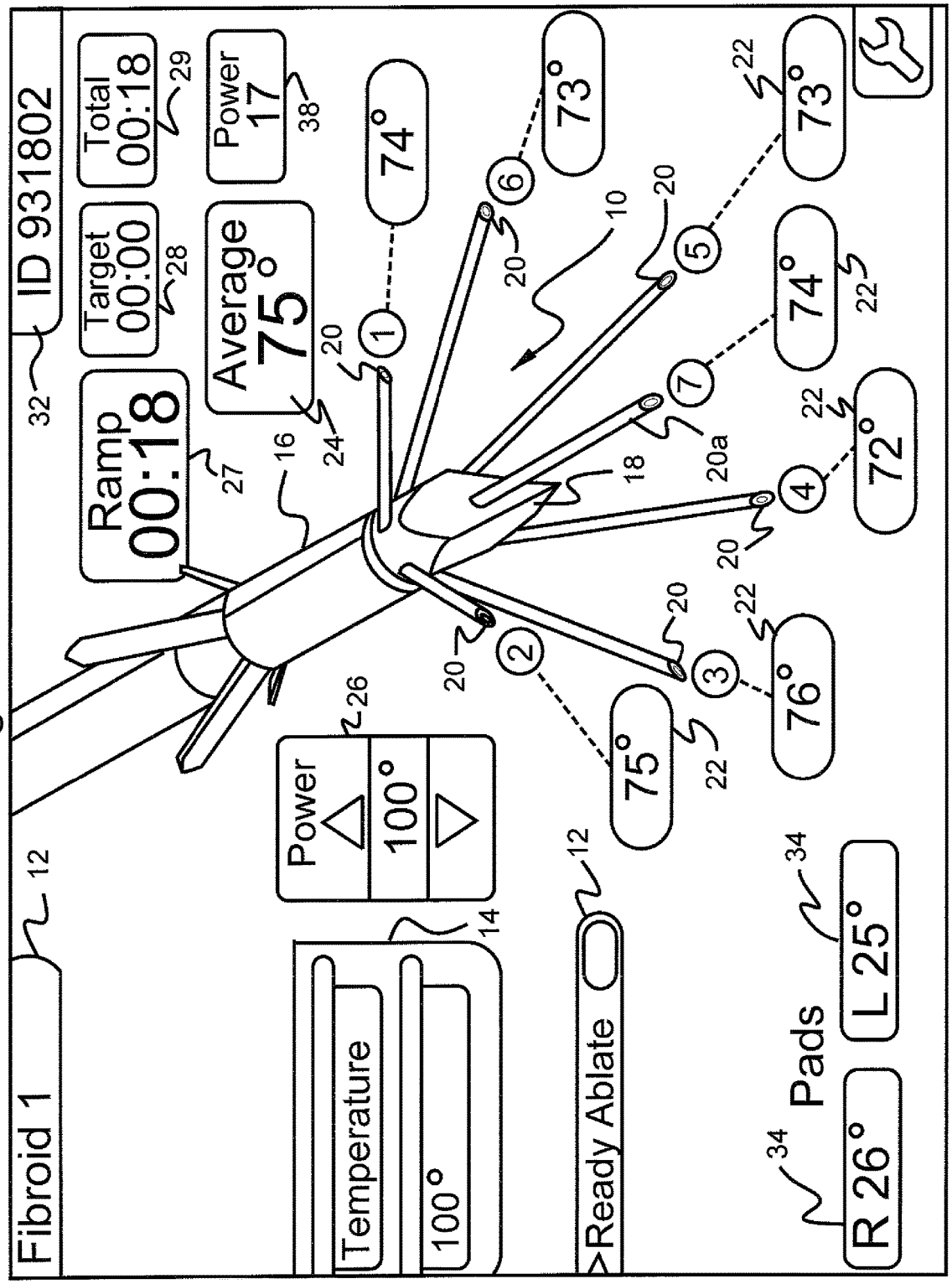
FIG. 25 shows the graphical user interface screen in which the menu "select procedure", the submenu "temperature" and the temperature of "100°" have been selected after 18 seconds into the ablation procedure, as shown as "ramp time" and "total time"; also shown is the average temperature and the temperature in tissue adjacent to each of the stylets of the ablation device, the power level submenu as well as the temperature in the right and left pad placed on a patient's legs.
Figure 26:
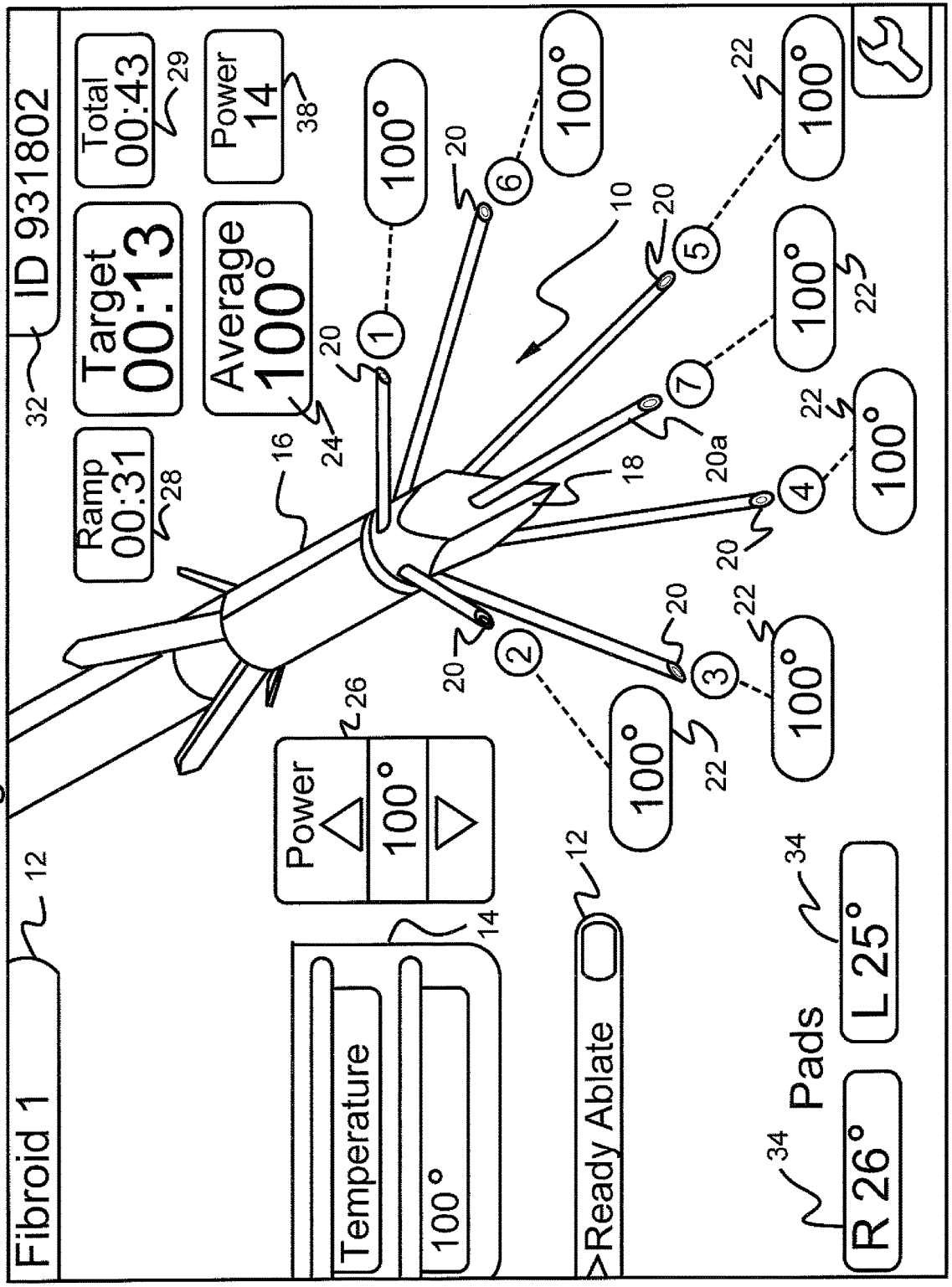
FIG. 26 shows the graphical user interface screen in which the menu "select procedure", the submenu "temperature" and the temperature of "100°" has been selected after 31 seconds into the ablation and 13 seconds at the target temperature for a total time of 43 seconds, as shown as "ramp time", "target time" and "total time"; also shown is the average temperature and the temperature in tissue adjacent to each of the stylets of the ablation device, the power level submenu as well as the temperature in the right and left pads placed on a patient's legs.

In accordance with the invention, the practitioner starts the ablation procedure by depressing and releasing a foot pedal. This activates the ablation device 16 to begin emission of radiofrequency energy through the stylets 20 into the site of the tissue mass. FIG. 25 shows that with the target temperature indicated on display 26 set at 100° C. and 18 seconds into the ablation procedure, as indicated by the "ramp" time display 27, six of the stylets show an average temperature indicated on display 24 of 75° C., the right and left pads show temperatures on display 34 of 26° C. and 25° C., respectively, and the power is indicated on display 38 at 17 watts. FIG. 26 shows that with the target temperature 26 set at 100° C. and 31 seconds into the ablation procedure, as indicated by the "ramp" time on display 27, and 13 seconds after reaching the target temperature indicated on display 26, as indicated by the "target" time display 28, for a "total" time indicated on display 29 of 43 seconds, all six of the stylets show that the target temperature 24 of 100° C. has been reached, the right and left pads 34 show temperatures of 26° C. and 25° C., respectively, and the power level 38 has decreased to 14 watts.

When the target temperature indicated on display 26 is reached, the power level 38 decreases. In accordance with the invention, there is provided a high power safety limit that shuts off the power if the target temperature 26 has not been reached in 1.5 minutes into the ablation procedure and the power has increased up to 200 watts. In addition, as another safety limit, it is provided that when the temperature of the three thermocouples in the right and left pads on the thighs of the patient reach 40° C., the pad temperature displays 34 turn yellow on the GUI. At 43° C., they turn red and at 44° C. radiofrequency emission is shut off.

Figure 27:
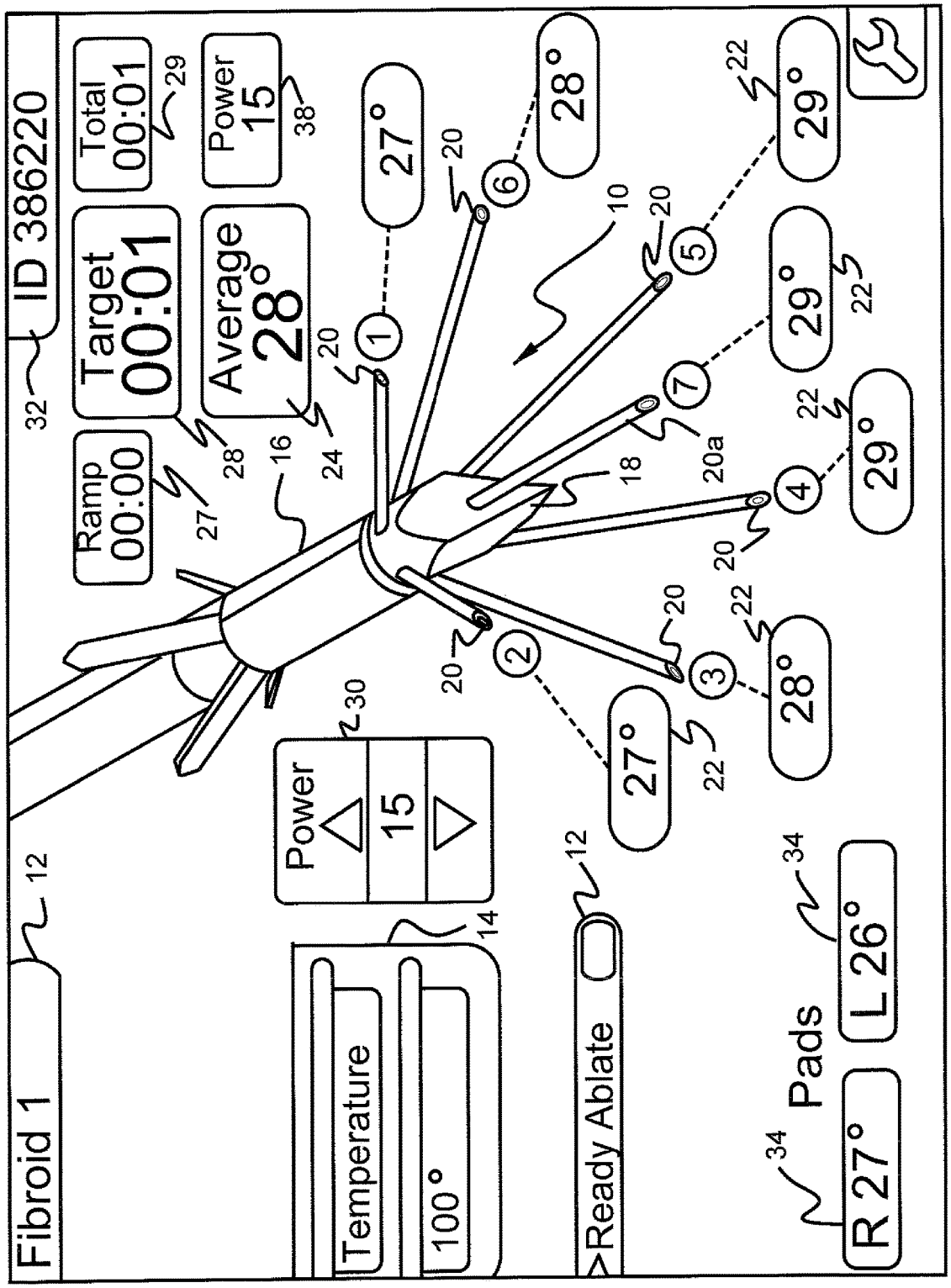
FIG. 27 shows the graphical user interface screen in which the menu "select procedure", the submenu "manual" and the target power level submenu of "15" has been selected after 1 second into the ablation. as shown as the target time; also shown is the average temperature and the temperature in tissue adjacent to each of the stylets of the ablation device as well as the temperature in the right and left pads.

FIG. 27 shows the operation of the ablation device using the menu 12 choice "manual" and presetting a target power level on display 30 at 15 watts, in which after one second, as indicated by the "ramp" time 27, the power level 38 has reached the target power level 30 of 15 watts.

Figure 28:
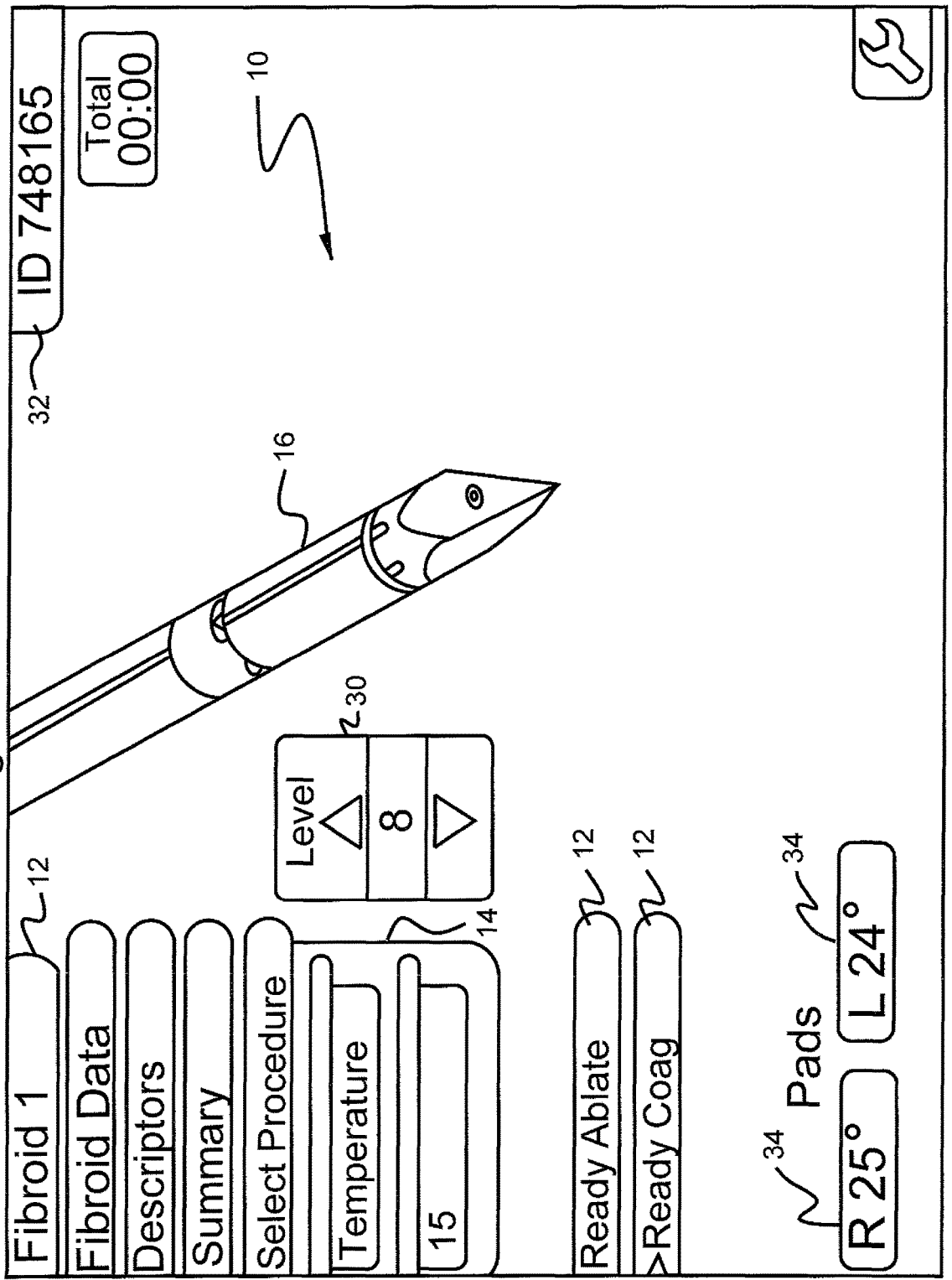
FIG. 28 shows the graphical user interface screen in which the menu "select procedure", the submenu "temperature" and 100° has been selected at the start of coagulation of the trocar entry path; also shown is the target power level submenu set at 8 watts.

In accordance with a preferred embodiment, and referring to FIGS. 28-31, coagulation of the track followed by the trocar to the uterine fibroid is achieved by selecting the menu 12 item "ready coag" and pressing and holding the foot pedal for the duration of the withdrawal of the trocar and coagulation of the path of entry of the trocar to the uterine fibroid. The coagulation procedure is performed by RF energy emitted from the trocar 18 of the ablation device 16 in which the stylets and anchors of the ablation device 16 have been retracted. FIG. 28 shows an illustration of the ablation device 16 with retracted stylets on GUI 10, a preset target temperature indicated on display 26 at 100° C., a target power level indicated on display 30 at 8 watts, and right and left pad temperatures of 25° C. and 24° C., respectively, indicated on the display 34.

Figure 29:
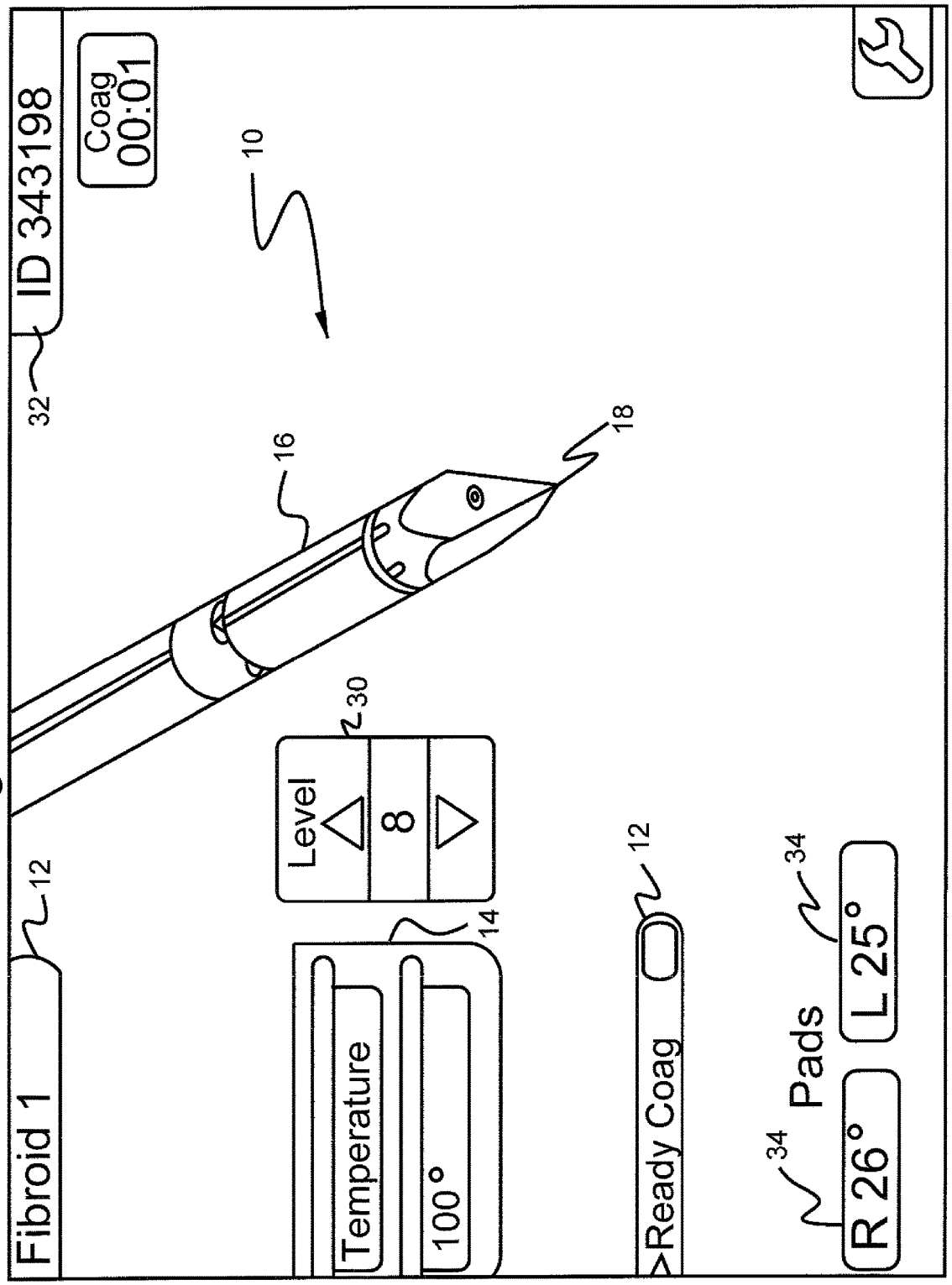
FIG. 29 shows the graphical user interface screen in which the menu "select procedure", the submenu "temperature" and 100° has been selected after 1 second of coagulation; also shown is the target power level submenu set at 8 watts.

After selecting "ready coag" the screen of FIG. 29 appears. FIG. 29 shows that the temperature in the right and left pads 34 has risen to 26° C. and 25° C., respectively, one second into coagulation. Here coagulation is done at a temperature of 100° C.

Figure 30:
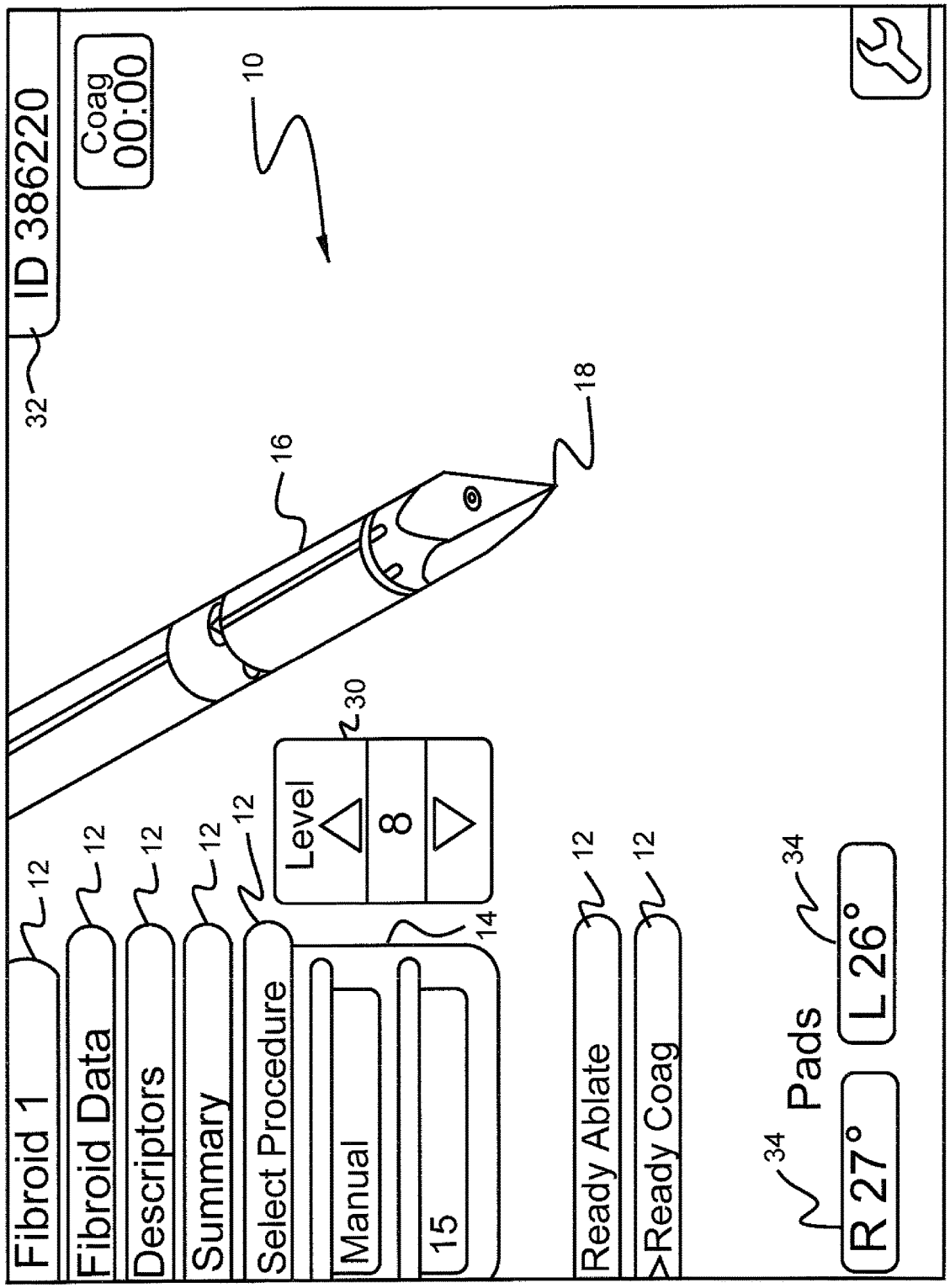
FIG. 30 shows the graphical user interface screen in which the menu "select procedure", the submenu "manual" and the target power level "15" has been selected at the start of coagulation.
Figure 31:
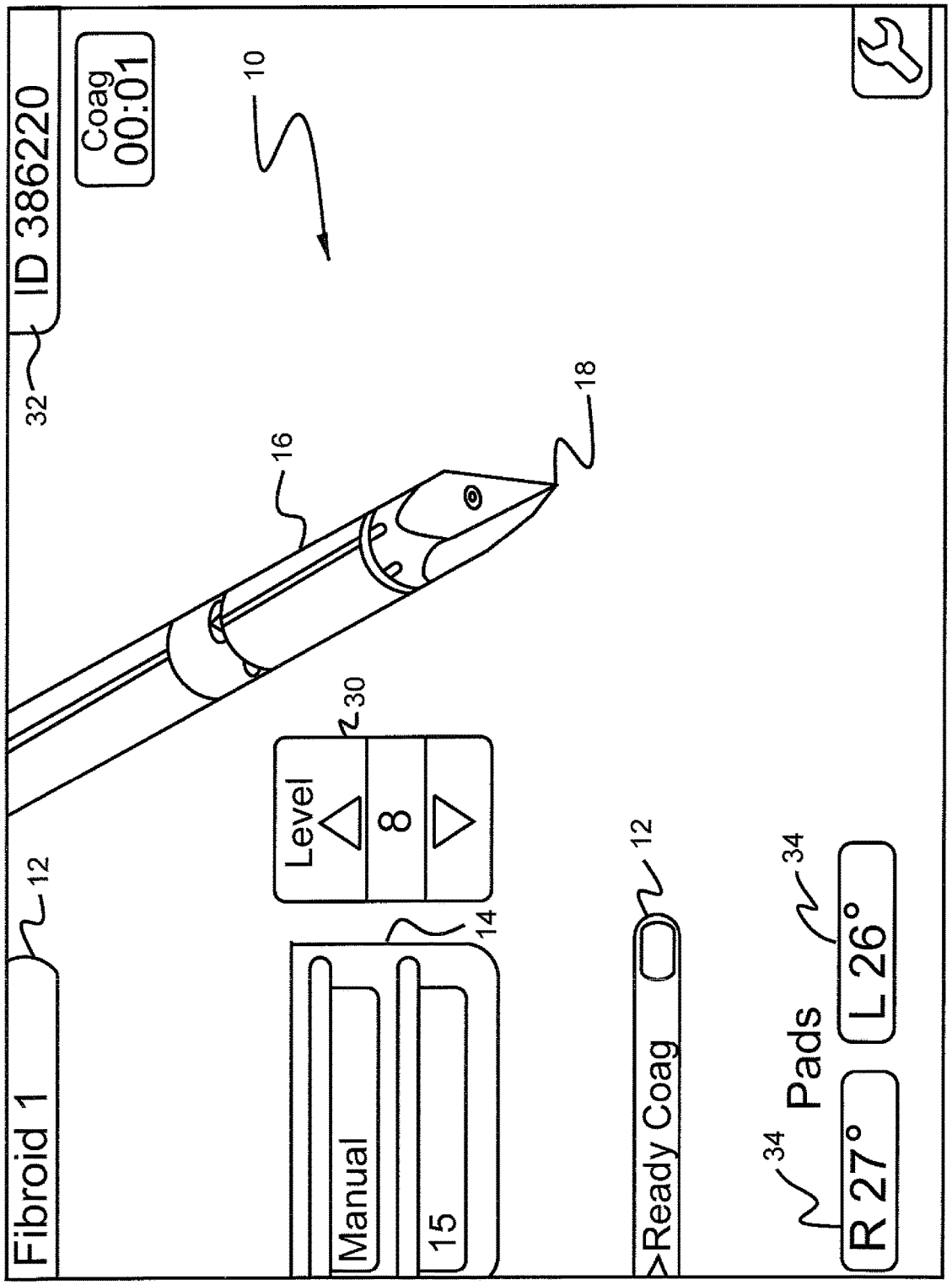
FIG. 31 shows the graphical user interface screen in which the menu "select procedure", the submenu "manual" and target power level of "15" has been selected after 1 second of coagulation.

Coagulation may also be done in the "Manual" mode with the power set to 15 W, as illustrated in FIG. 30. FIG. 30 shows the operation of the ablation device using the menu 12 choice "manual" and a preset target power level 30 rather than a preset target temperature. The target power level on indicator 30 is set to 8 watts prior to the start of coagulation of the trocar track ("coag" time: 0 seconds) and the temperature of the right and left pads, indicated on display 34, is 27° C. and 26° C., respectively.

Figure 32:
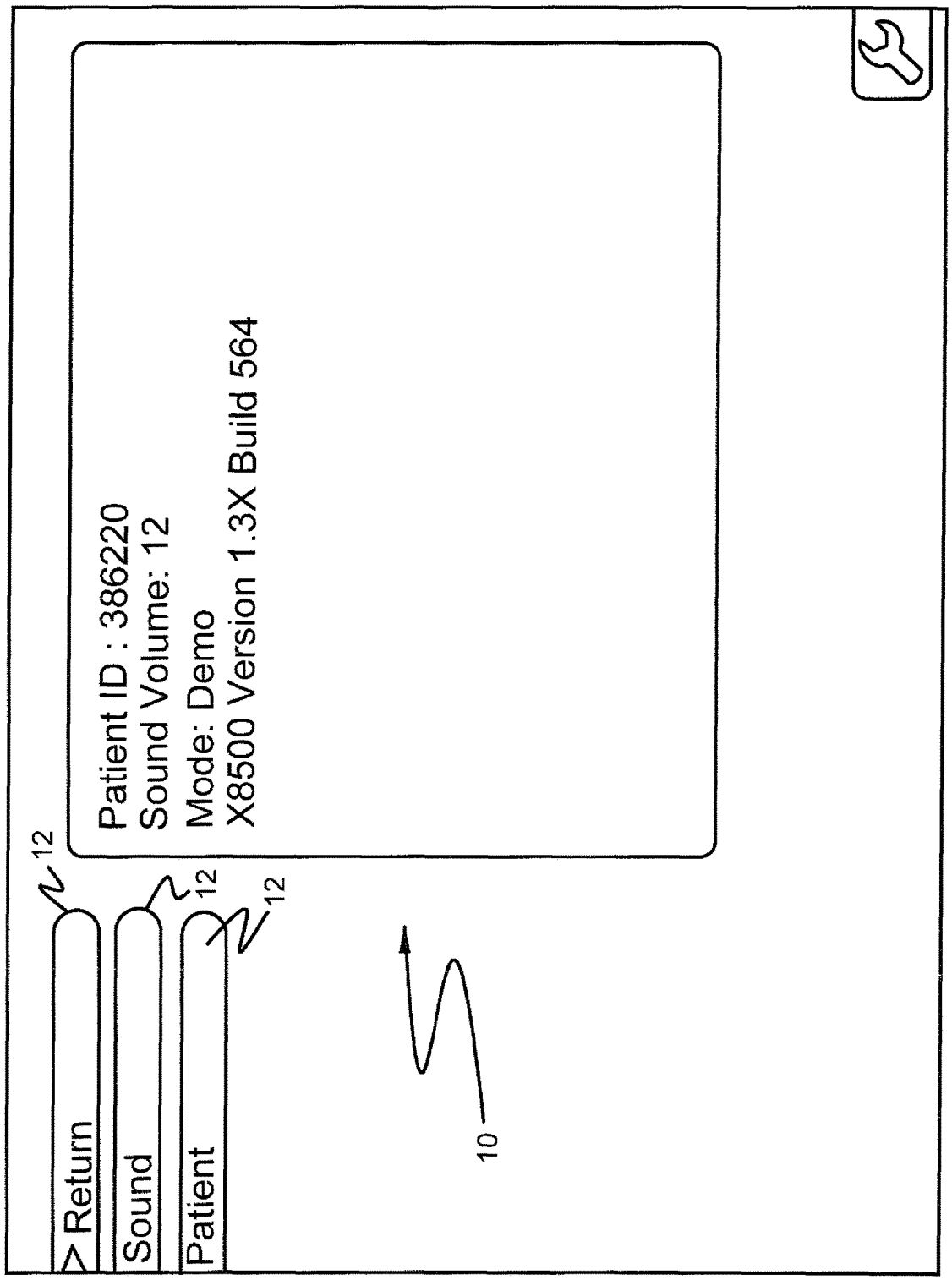
FIG. 32 shows the graphical user interface screen in which the menus "return", "sound", and "patient" are displayed and "return" has been selected showing patient and computer software information.
Figure 33:
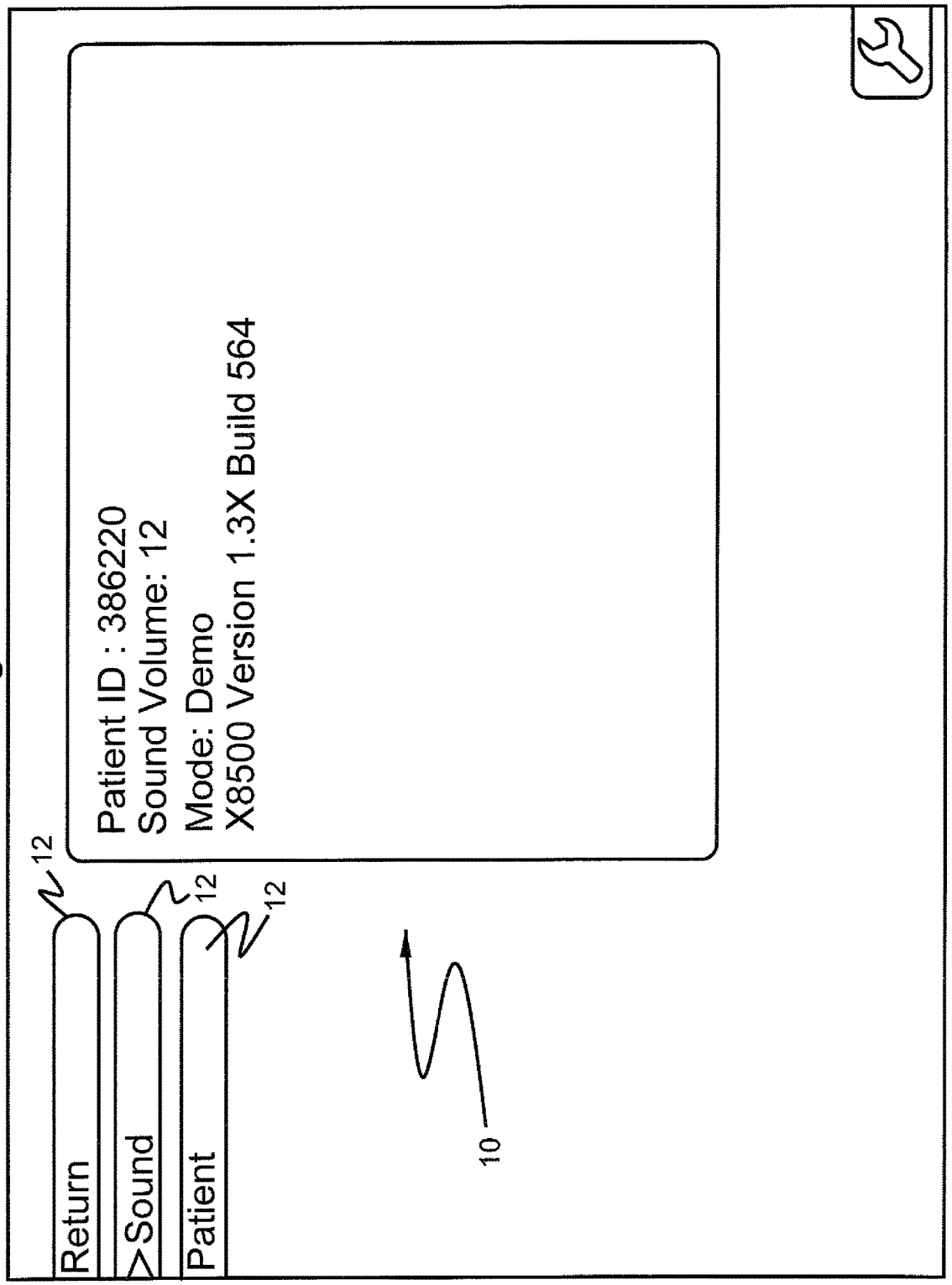
FIG. 33 shows the graphical user interface screen in which the menus "return", "sound", and "patient" are displayed and the navigational tool has scrolled to the "sound" menu.

In accordance with the invention and referring to FIGS. 32-40, when the surgical procedure is completed, the practitioner can select the menu 12 "return" item, which displays on the GUI 10 patient identification number and various features of the computer software program, such as sound volume, software mode and software version (FIG. 32). In addition, the computer software program contains menu choices for keeping patient records and allows for the selection of text in different languages. Notes may also be kept by dictation in different "sound volumes" associated with the patient.

Figure 34:
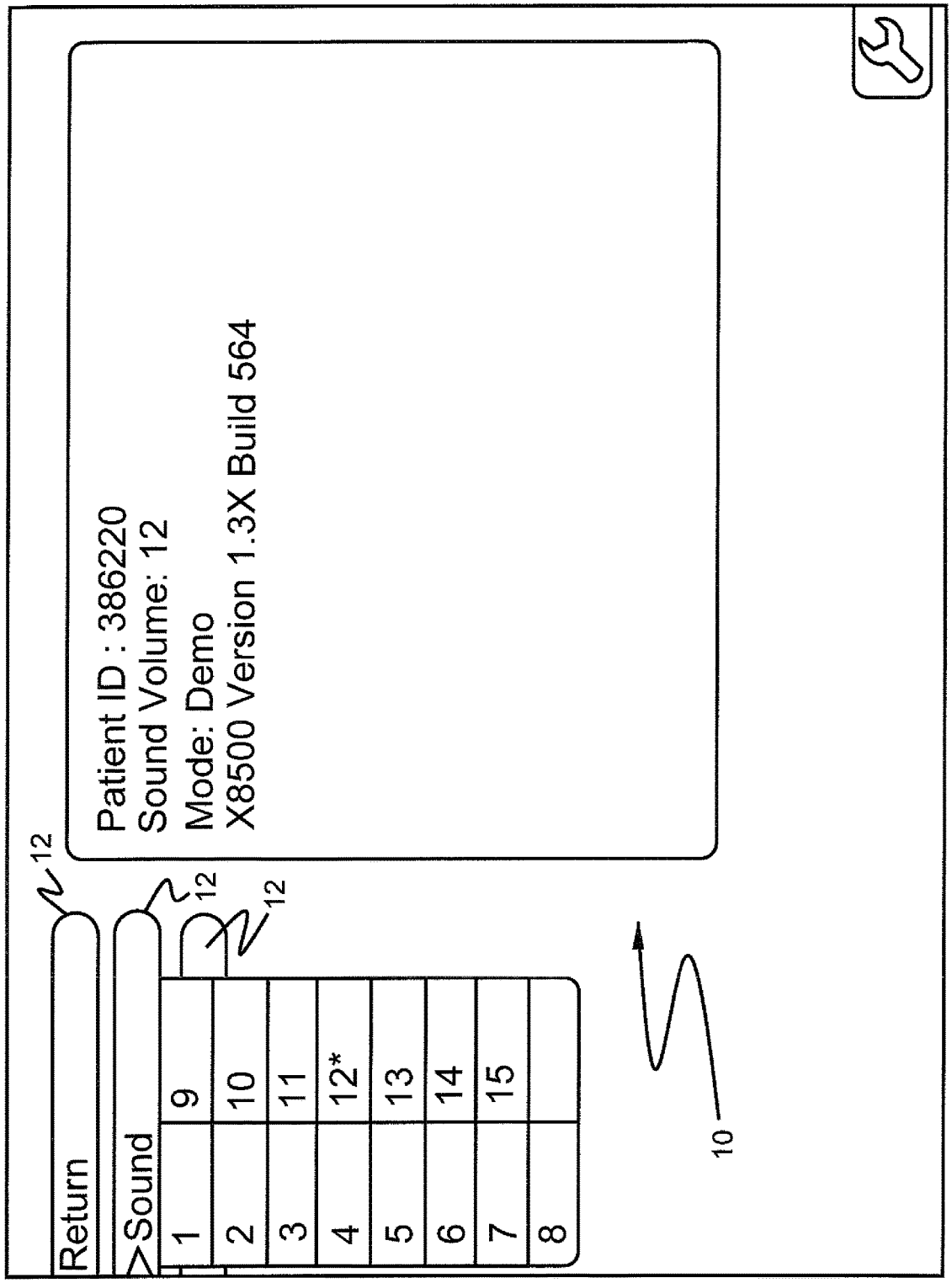
FIG. 34 shows the graphical user interface screen in which submenus"1" through "15" are displayed after selecting the "sound" menu and showing the sound volume selected as "12"
Figure 35:
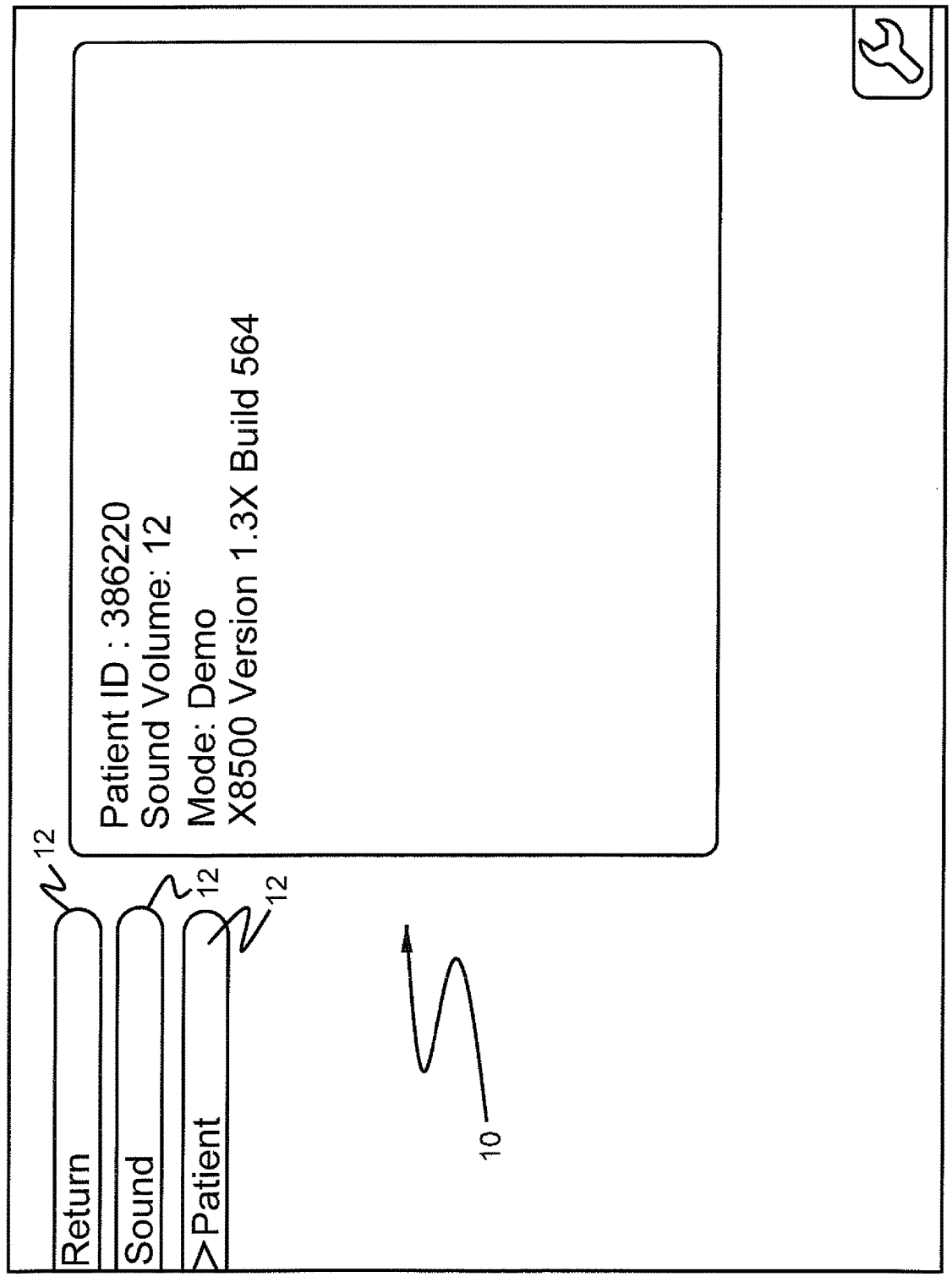
FIG. 35 shows the graphical user interface screen in which the menus "return", "sound", and "patient" are displayed and the navigational tool has scrolled to the "patient" menu.
Figure 36:
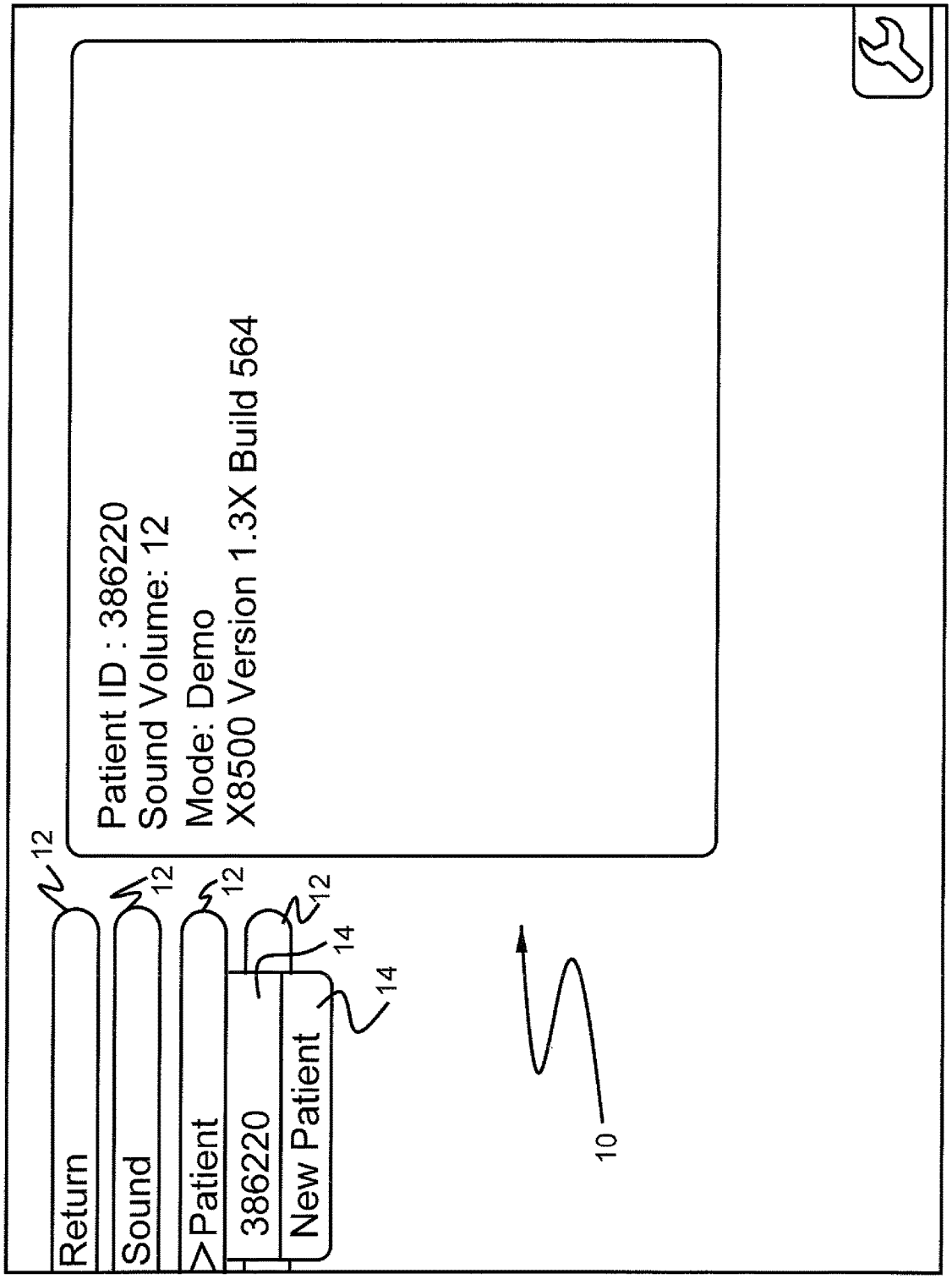
FIG. 36 shows the graphical user interface screen in which the submenu identification number of a patient is displayed after selecting the "patient" menu.
Figure 37:
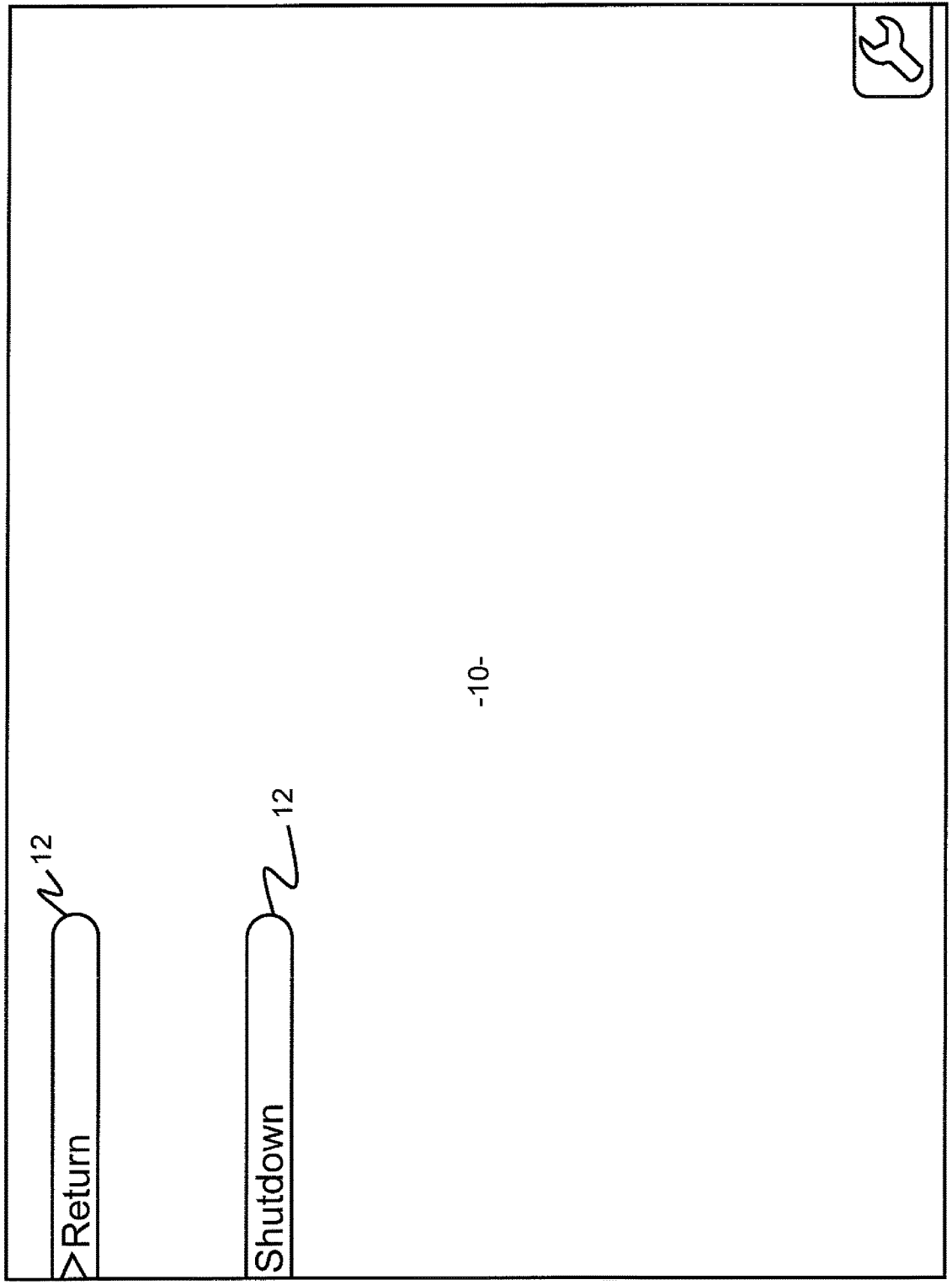
FIG. 37 shows the graphical user interface screen in which the menus "return" and "shutdown" are displayed.
Figure 38:
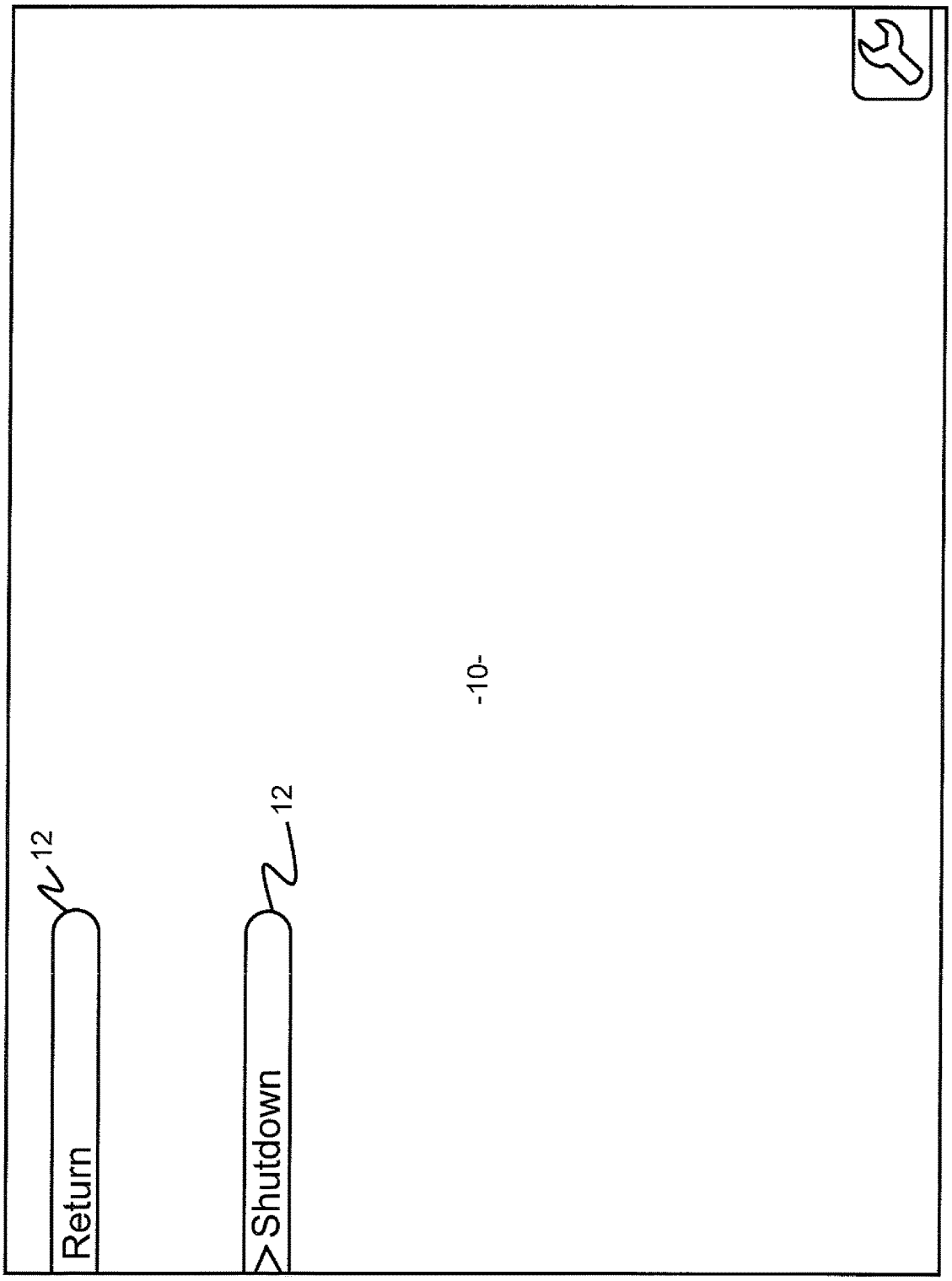
FIG. 38 shows the graphical user interface screen in which the menus "return" and "shutdown" are displayed and "shutdown" is selected.
Figure 39:
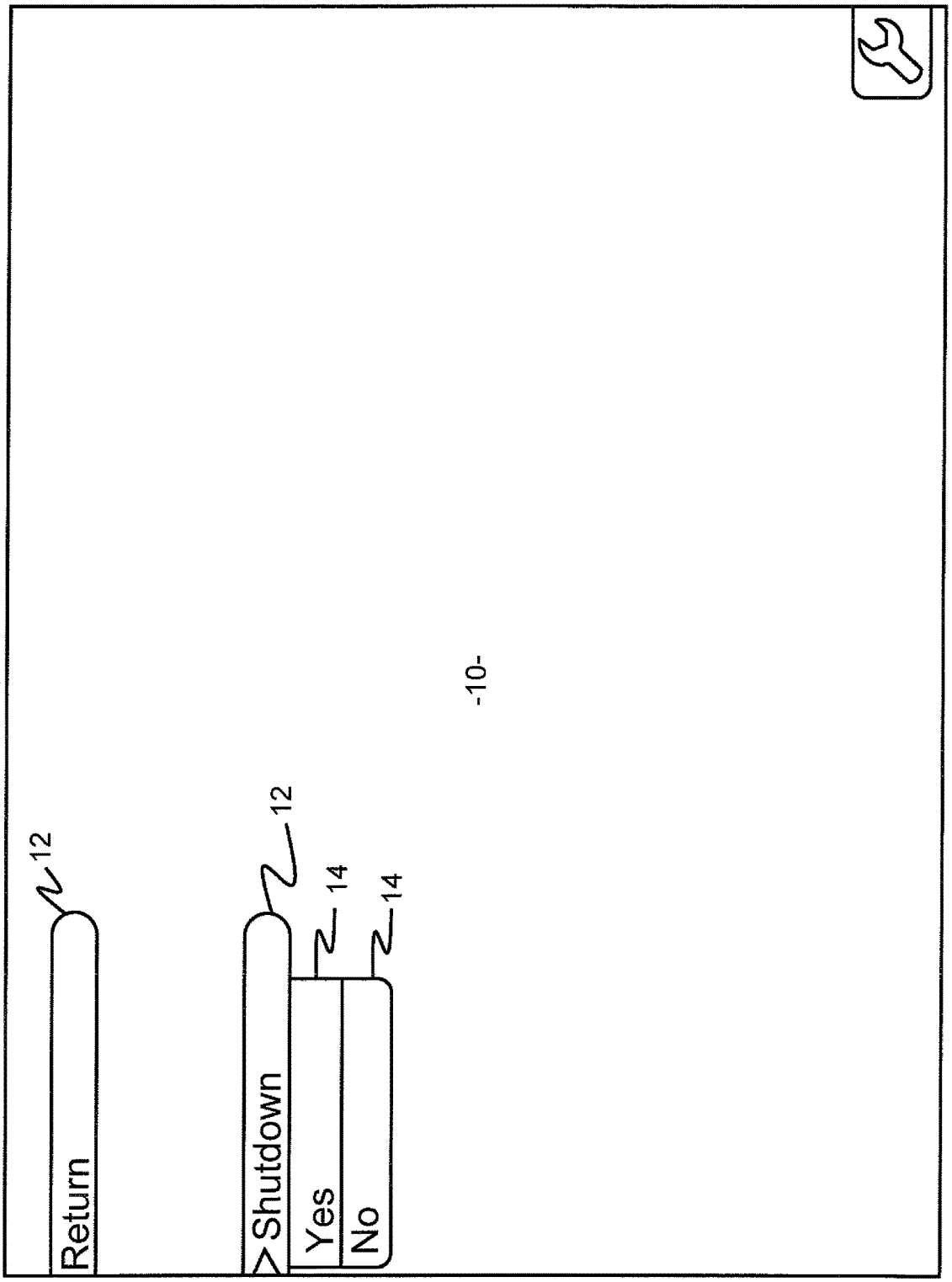
FIG. 39 shows the graphical user interface screen in which the menus "return" and "shutdown" are displayed, "shutdown" is selected and the submenus "yes" and "no" are displayed.
Figure 40:
FIG. 40 shows the graphical user interface screen in which the computer software program has been shut down after selecting "yes" from the "shutdown" menu.

For example, by selecting the "sound" menu item 12 (FIG. 33), a series of sound volumes are shown from which the practitioner can select. FIG. 34 shows the selection of sound volume 12. By selecting the "patient" menu 12 (FIG. 35), the practitioner can select a patient identification number or enter a new patient identification number (FIG. 36). By selecting the "return" menu 12 again (FIG. 37), the practitioner can scroll to a "shutdown" menu 12 (FIG. 38), select the "shutdown" menu 12, and then select from the submenus 14 "yes" or "no" to shut down the computer program (FIG. 39). FIG. 40 shows the GUI after the computer program has been shut down.

An exemplary system for implementing the above invention is illustrated in FIG. 1b. Generally, the system 110 comprises a computer 112. Computer 112 may be any control device, such as a microprocessor, personal computer or a more powerful or less powerful computer with a typical personal computer-type operating system. Computer 112 includes a display screen 114, which may optionally be a touchscreen to provide a second means of navigation.

Personal computer 112 also incorporates software 116. Software 116 may be of any type for use on any suitable computing device, and which may be easily written by a programmer of ordinary skill in the art who is informed by this specification. The software is responsive to produce images illustrated in the drawings and stored in a memory 118 of computer 112. The software performs the navigation functions described above, being responsive to touchscreen entry and/or scroll and select buttons 23 and 25 on ablation instrument 1.

Computer 112 communicates with ablation instrument 1 through an interface board 120 which is coupled to scroll and select buttons 23 and 25. Likewise, in response to operation by touching on display screen 114 or operation of scroll and select buttons 23 and 25, computer 112 may cause RF generator 122 to apply power to the trocar point for ablation. In response thereto, thermocouples on stylets 20 will generate temperature indicating signals which are coupled through suitable interface electronics to computer 112, allowing the computer to control application of RF generator by RF generator 122, to display temperature information, operate alarms, to terminate the application of RF energy, and to perform any other design controls in response thereto, for example as described above.

In accordance with U.S. Pat. No. 6,840,935 issued to Lee on Jan. 11, 2005, uterine ablation may be implemented with imaging provided through the use of a laparoscope imaging arrangement and an ultrasound imaging device. The images generated by the laparoscope and the ultrasound device are provided on separate monitors.

In accordance with the present invention, it is contemplated that the display of the present invention, as detailed above, may include touchscreen controls and/or menu options for controlling other devices. For example, the display may provide for navigation to a control menu for controlling display characteristics for the ultrasound viewing device, a control menu for selecting metering functions for inclusion on the display, such as heartbeat, or for selection between ultrasound and laparoscopic images.

The inventive system may also incorporate means for varying the various menu functions described above incorporated into the software which controls the system. Such means may comprise accessing menu choices and display options using a keyboard.

In accordance with a particularly preferred embodiment of the present invention, the display of menu options (and the other GUI elements, or some of them) as detailed in FIGS. 1-40, may also be incorporated into the display of, for example, the ultrasound image used by the physician. Other types off images may also be employed. More particularly, with reference to FIG. 41, the inventive system 210 utilizes an ablation probe 212. Ablation probe 212 includes a multi-button keypad 214, for example with scroll and select switches.

In the manner of the earlier embodiment, temperature signals and keypad control information is coupled to a computer interface 216 which sends this information to personal computer 218. Personal computer 218 drives a computer display 220 which includes a navigation menu 222 of the type described above in connection with FIGS. 1-40.

As detailed above in connection with FIGS. 1-40, personal computer 218 through interface board 224 controls ablation energy source 226. At the same time, an ultrasound probe 228 coupled to an ultrasound machine 230 provides ultrasound image information to interface 224 which in turn provides this information to personal computer 218 for display on computer display 220.

Figure 41:
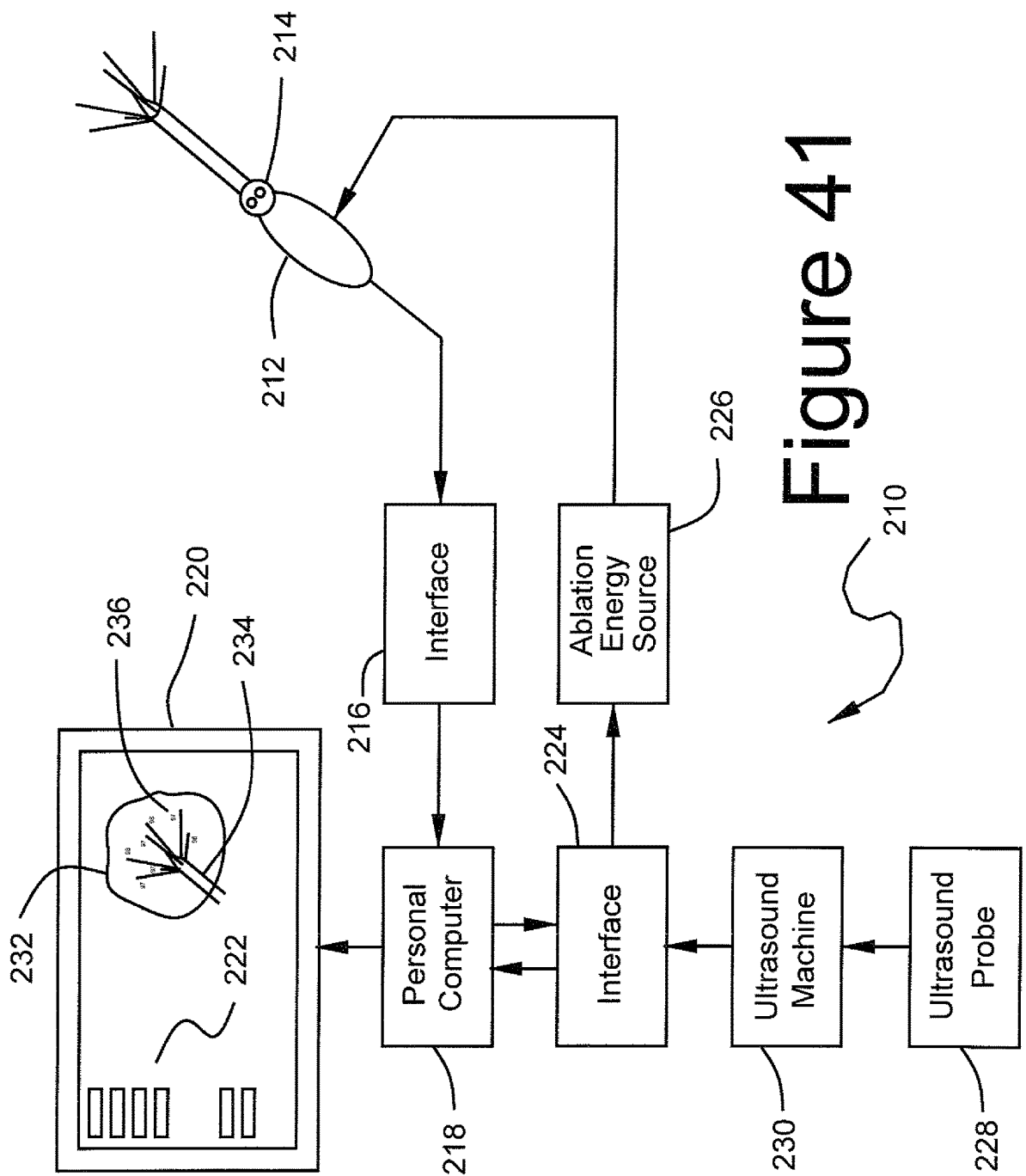
FIG. 41 illustrates an alternative inventive system where imaging data is displayed on the GUI.

Using the system of FIG. 41, the surgeon may concentrate on a single monitor displaying both ultrasound, and device performance information and a means for control of the system. More particularly, computer display 220 displays, for example, the fibroid 232 being operated on, an image 234 of probe 214 and an image 236 of temperature data. The positioning of the images 234 and 236 may be done by the computer using a pattern matching or other strategy.

Figure 42:
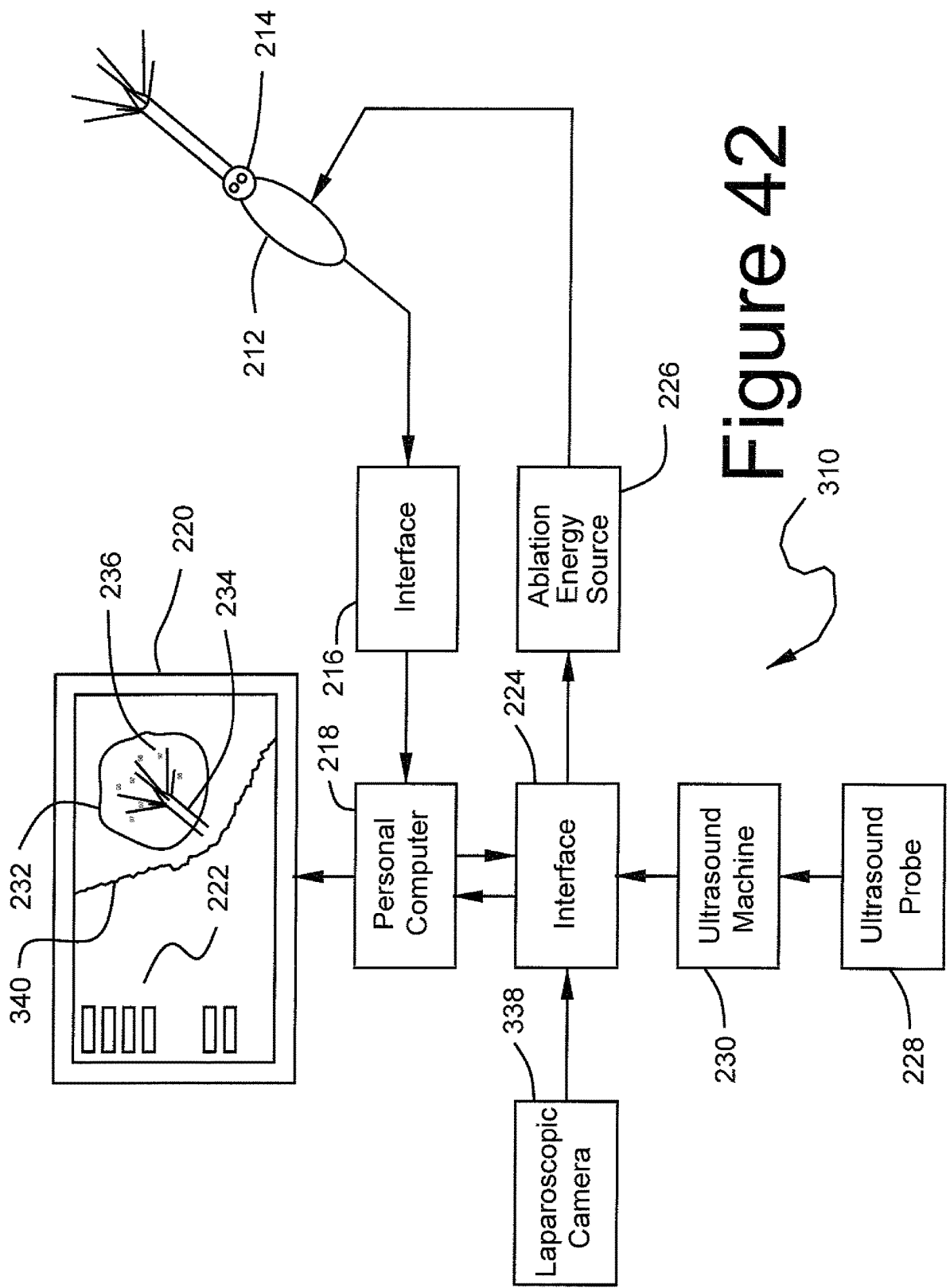
FIG. 42 illustrates an alternative inventive system where imaging data from two different image sources is merged and displayed on the GUI.

A most preferred embodiment of the present invention is illustrated in FIG. 42. The operation of the system 310 of FIG. 42 is substantially the same as that of the system in FIG. 41, except for the addition and integration of an image from a laparoscope.

More particularly, a laparoscopic camera 338 is coupled to interface 224. Camera 338 produces an image of the outside of the uterus resulting in display of an image 340 of the uterus on computer display 220 superimposed over the image 232 of the fibroid obtained using ultrasound. It is noted that images 232 and 340 are positioned in the same manner as the fibroid and the uterus are positioned in the patient, thus giving a more complete picture of the state of the surgery.

It will be appreciated by those skilled in the art that changes can be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A system for remote control of an ablation device for ablating a tissue mass in a patient, comprising:
   (a) a first imaging device comprising an ultrasound probe having a first image output, said ultrasound probe coupling to an ultrasound machine, said ultrasound machine coupling to an interface and providing ultrasound image information to said interface, said first imaging device being configured for insertion into the patient and for contacting tissue in proximity to the tissue mass to image an area being subject to surgery;

(b) a second imaging device comprising a laparoscopic camera having a second image output, said laparoscopic camera coupling to said interface and providing laparoscopic image information to said interface, said second imaging device being configured for insertion into the patient and into proximity to the tissue mass to image said area being subject to surgery;

(c) a computer coupled to the interface to receive said first and second image outputs and merge said first and second image outputs into a unitary image output representing a unitary image having a visual representation of said ablation device and a visual representation of the area being subject to surgery such that relative positioning of the visual representations of the ablation device and the area are superimposed and maintained relative to one another;

(d) a computer software program, resident in said computer on a non-volatile memory device, for causing said computer to generate a graphical user interface which displays a series of menus and submenu items;

(e) said ablation device coupled to said computer, said ablation device having an operator handle configured and dimensioned to be grasped by the surgeon, said interface controlling operation of an ablation energy source coupled to said ablation device;

(f) a navigational tool fixed to said operator handle for interacting with said computer software;

(g) second software, resident in said computer on a non-volatile memory device, for receiving and displaying information received from said ablation device and/or for controlling operation of said ablation device; and (h) a display coupled to said computer for displaying said graphical user interface and said unitary image.

2. The system of claim 1, wherein said ablation device is a radio frequency ablation device used during a surgical procedure, said radio frequency ablation device comprising a radiofrequency source and a plurality of stylets for conducting radiofrequency radiation from the radiofrequency source;

said navigational tool comprising a scroll button and a select button, said scroll button allowing the practitioner to scroll through the series of menus and submenu items, as indicated by a scroll position indicator on said graphical user interface, said select button allows the practitioner to select from the series of menus and submenu items displayed on said graphical user interface and implement an action or display a further selection from the series of menus and submenu items on said graphical user interface.

3. The system of claim 2, further comprising a foot pedal coupled to the radiofrequency source to allow the practitioner to send radiofrequency energy to the plurality of stylets of the ablation device in order to ablate or coagulate the tissue mass of the patient.

4. The system of claim 3, wherein the plurality of stylets of the ablation device is adapted to deliver an electrical current to the tissue mass in the patient and to a right and a left pad placed atop the right and the left leg, respectively, of the patient, said system further comprising measurement structure associated with the plurality of stylets for measuring the temperature of the tissue mass adjacent to the plurality of stylets of the ablation device, the highest temperature reached by the tissue mass adjacent to the plurality of stylets of the ablation device being displayed on the graphical user interface.

5. The system of claim 2, wherein the series of menus are selected from the group consisting of fibroid data, descriptors, summary, select procedure, ready ablate and ready coag choices.

6. The system of claim 5, wherein the fibroid data menu includes submenu choices selected from the group consisting of number, diameter, position and type.

7. The system of claim 6, wherein the position choices are selected from the group consisting of anterior, posterior and lateral positions.

8. The system of claim 7, wherein the anterior, posterior and lateral position choices each include submenus selected from the group consisting of midline, right and left choices.

9. The system of claim 8, wherein the submenu for midline, right and left choices each include a further submenu selected from the group consisting of fundal, miduterine, lower segment and cervical choices.

10. The system of claim 9, wherein the submenu for fundal, mid-uterine, lower segment and cervical choices each include a further submenu selected from the group consisting of intramural, subserosal, submucous 1 and submucous 2 choices.

11. The system of claim 5, wherein the select procedure menu includes the submenus selected from the group consisting of temperature, manual and impedance choices.

12. The system of claim 4, wherein the selection of one of said menus and one of said submenus, and the radiofrequency radiation enabled by the foot pedal enables ablation of the tissue mass by the ablation device.

13. The system of claim 12, wherein the graphical user interface displays the temperature of the tissue mass adjacent to each of the plurality of stylets, and wherein an average temperature of the tissue mass is calculated from the temperatures associated with the tissue adjacent two or more of the plurality of stylets ablating the tissue mass, said average temperature displayed on the graphical user interface.

14. The system of claim 13, wherein time elapsed from the start of ablation is displayed as ramp time on the graphical user interface; time elapsed at the preset target temperature is displayed as target time on the graphical user interface, said target time ranging from about 10 seconds to about 20 minutes; and total time elapsed from the start of ablation to the end of ablation is displayed as total time on the graphical user interface.

15. The system of claim 11, wherein the manual choices include target power levels ranging from about 10 watts to about 100 watts.

16. A system for remote control of an ablation device during a surgical procedure, comprising:

(a) a first imaging device comprising an ultrasound probe having a first image output, said ultrasound probe coupling to an ultrasound machine, said ultrasound machine coupling to an interface and providing ultrasound image information to said interface, said first imaging device being configured for insertion into the patient and for contacting tissue in proximity to the tissue mass to image an area being subject to surgery;

(b) a second imaging device comprising a laparoscopic camera having a second image output, said laparoscopic camera coupling to said interface and providing laparoscopic image information to said interface, said second imaging device being configured for insertion into the patient and into proximity to the tissue mass to image said area being subject to surgery;

(c) a computer coupled to the interface to receive said first and second image outputs and merge said first and second image outputs into a unitary image output representing a unitary image having a visual representation of said ablation device and a visual representation of the area being subject to surgery such that relative positioning of the visual representations of the ablation device and the area are superimposed and maintained relative to one another;

(d) a computer software program, resident in said computer for generating a graphical user interface which displays a series of menus and submenu items;

(e) said ablation device coupled to said computer, said ablation device having an operator handle, said interface controlling operation of an ablation energy source coupled to said ablation device;

(f) a navigational tool mounted on said operator handle for interacting with said computer software;

(g) software, resident in said computer, for receiving and displaying information received from said ablation device and/or for controlling operation of said ablation device; and (h) a display coupled to said computer for displaying said graphical user interface and said unitary image.

17. A system as in claim 16, wherein said navigational tool comprises at least one select button which has one raised dot on a top surface of said select button and at least one scroll button.

* * * * *